(12) United States Patent
Hirao et al.

(10) Patent No.: US 6,626,851 B2
(45) Date of Patent: Sep. 30, 2003

(54) BLOOD-COLLECTION POSITION INDICATOR

(75) Inventors: Etsuo Hirao, Kyoto (JP); Takashi Tsujii, Kyoto (JP); Yoshiharu Sato, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 10/290,968

(22) Filed: Nov. 8, 2002

(65) Prior Publication Data

US 2003/0073933 A1 Apr. 17, 2003

Related U.S. Application Data

(62) Division of application No. 09/687,547, filed on Oct. 13, 2000, now Pat. No. 6,503,210.

(30) Foreign Application Priority Data

Oct. 13, 1999 (JP) .............................................. 11-290785
Mar. 1, 2000 (JP) ........................................ 2000-056360
May 9, 2000 (JP) ........................................ 2000-135818

(51) Int. Cl.⁷ .............................................. B65D 81/00
(52) U.S. Cl. ........................................ 600/576; 606/182
(58) Field of Search ................................ 600/576, 182, 600/573, 584, 322, 583; 606/181, 182; 422/73

(56) References Cited

U.S. PATENT DOCUMENTS 3,626,929 * 12/1971 Sanz et al. .................. 600/583

4,595,021   6/1986 Shimizu et al.

(List continued on next page.)

FOREIGN PATENT DOCUMENTS

| EP | 0 671 146 | 8/1994 | |
| JP | 406114039 | * 4/1994 | ............ A61B/5/14 |
| JP | 10-295675 | 11/1998 | |
| WO | WO 91/05511 | 5/1991 | |
| WO | WO 92/03174 | 3/1992 | |
| WO | WO 97/42883 | 11/1997 | |

*Primary Examiner*—Teresa Walberg
*Assistant Examiner*—L Fastovsky
(74) *Attorney, Agent, or Firm*—Merchant & Gould P.C.

(57) ABSTRACT

A blood-collection position indicator facilitating blood collection is provided. An adhesive layer is positioned on the back face of a substrate portion having a convex cross section and a circular planar shape, and at its center, a through hole going through the substrate portion and the adhesive layer is provided to serve as a blood collection hole, thus obtaining a blood-collection position indicator. In the blood-collection position indicator, the protruding portion serves as an attachment part to be attached to the tip of a lancet device, and the protruding portion is inserted into a hole of the tip of the lancet device, thus attaching the blood-collection position indicator to the tip of the lancet device. Adhesive strength of the adhesive layer to the skin is set to be stronger than attachment strength of the attachment part to the tip of the lancet device. Consequently, only the first blood-collection position indicator remains on the skin after the lancet device is used. By using the blood-collection position indicator as a mark, blood can be collected from the blood collection hole.

9 Claims, 34 Drawing Sheets

U.S. PATENT DOCUMENTS

| | | | |
|---|---|---|---|
| 4,608,997 | * | 9/1986 | Conway ..................... 600/576 |
| 4,653,513 | | 3/1987 | Dombrowski |
| 4,677,979 | | 7/1987 | Burns |
| 4,920,977 | * | 5/1990 | Haynes ..................... 600/583 |
| 4,978,342 | | 12/1990 | Heimreid |
| 5,163,442 | | 11/1992 | Ono |
| 5,279,294 | * | 1/1994 | Anderson et al. ........... 600/322 |
| 5,385,571 | * | 1/1995 | Morita ..................... 606/181 |
| 5,569,223 | | 10/1996 | Wandell et al. |
| 5,570,700 | | 11/1996 | Vogeler |
| 5,636,640 | | 6/1997 | Staehlin |
| 5,700,695 | | 12/1997 | Yassinzadeh et al. |
| 5,792,052 | | 8/1998 | Isaacson |
| 5,800,781 | * | 9/1998 | Gavin et al. ................... 422/73 |
| 5,913,833 | | 6/1999 | Elstrom et al. |
| 5,951,582 | * | 9/1999 | Thorne et al. ............. 606/182 |
| 6,004,278 | | 12/1999 | Botich et al. |
| 6,071,294 | * | 6/2000 | Simons et al. ............. 606/181 |
| 6,080,116 | * | 6/2000 | Erickson et al. ............ 600/573 |
| 6,099,484 | | 8/2000 | Douglas et al. |
| 6,206,841 | * | 3/2001 | Cunningham et al. ...... 600/584 |
| 6,315,738 | | 11/2001 | Nishikawa et al. |
| 6,379,317 | * | 4/2002 | Kintzig et al. ............. 600/573 |
| 6,409,740 | * | 6/2002 | Kuhr et al. ................. 600/182 |
| 6,503,210 | * | 1/2003 | Hirao et al. ................ 600/576 |

* cited by examiner

BLOOD-COLLECTION POSITION INDICATOR

This application is a divisional of application Ser. No. 09/687,547, filed Oct. 13, 2000, now U.S. Pat. No. 6,503,210, which application(s) are incorporated herein by reference.

BACKGROUND OF THE INVENTION

1. Field of the Invention

The present invention relates generally to a blood-collection position indicator serving as a mark for allowing a blood collecting instrument or the like to be guided easily in blood collection from a finger or the like.

2. Related Background Art

Currently, as a method of measuring a blood glucose level (a glucose concentration) through blood collection at home by diabetics without requiring them to visit a medical institution, for instance, the following method has been practiced widely, in which a lancet and a simplified glucose measuring instrument are used.

The above-mentioned lancet is a disposable needle or cutting tool used for puncturing the skin of a patient, which is set in its own ejection device called a "lancet device" and then is used. Further, for example, as shown in FIG. 23, a simplified glucose measuring instrument 6 includes a disposable strip 61 and a meter 62 used exclusively for measuring a glucose content with the disposable strip 61 being set therein. The disposable strip 61 has a specimen supply section and a reagent section containing glucose oxidase or the like that reacts specifically with glucose contained in a specimen. Generally, the strip 61 has a capillary structure so as to allow a supplied specimen to be transported.

Using the lancet and the measuring instrument, for instance, glucose can be measured as follows. Initially, the lancet is set inside a lancet device, and a tip of the lancet device is brought close to a skin surface. Then, the lancet thus set is ejected to puncture the skin and blood is squeezed out from the punctured site to form a blood "pool". Then, when the tip of the strip 61 of the measuring instrument 6 is brought into contact with the blood in the punctured site, the strip 61 absorbs the blood by a capillary phenomenon and transports it to the reagent section. In the reagent section, glucose in the blood and the reagent start to react with each other. After the glucose and the reagent are allowed to react with each other for a certain period, the meter 62 detects the reaction product of them and converts it into a glucose concentration, which then is displayed on a monitor.

However, for diabetics having total blindness or weak eyesight because of complication of diabetes, patients who cannot carry out fine manual operations, or the like, for instance, it is difficult to bring the tip of the strip 61 into contact with the blood in the punctured site punctured with a lancet or to carry out the aforementioned series of operations alone.

In order to solve such problems, for example, JP 10-295675 A discloses a finger band for blood collection provided with a blood collection hole and a retaining part for holding a finger. When this finger band is used, the blood collection hole functions as a guide for a blood-collecting needle. Therefore, it is easy to bring the blood-collecting needle into contact with a target position on the skin using the sense of touch. In addition, blood can be dropped from the blood collection hole directly on a diagnostic device.

However, such a finger band has a difficulty in being attached to or detached from the punctured site. It has been required to puncture the skin more easily and to provide blood for a measuring device such as the simplified glucose measuring instrument easily.

SUMMARY OF THE INVENTION

The present invention at least in its preferred embodiments is intended to provide a blood-collection position indicator serving as a mark for a punctured site on the skin and allowing blood to be collected from the punctured site easily.

In order to achieve the above-mentioned object, the present inventors found the following two blood-collection position indicators.

A first blood-collection position indicator of the present invention includes an adhesive portion to be stuck to skin, an attachment part, into which a tip of a lancet device including a lancet is attached, and a blood collection hole, wherein the blood-collection position indicator is attached to the tip of the lancet device in a state where the lancet is arranged to pass through the blood collection hole before the lancet device is used, and wherein the adhesive strength of the adhesive portion to the skin is stronger than the attachment strength of the attachment part to the tip of the lancet device, whereby in use, the blood-collection position indicator adheres to and remains on the skin after the lancet device is used.

When using such a first blood-collection position indicator, a patient can recognize a punctured site on the skin through the blood-collection position indicator by the sense of touch without relying on the visual sense. The patient can bring the tip of a strip in the aforementioned measuring instrument into contact with blood in the blood collection hole of the blood-collection position indicator, thus collecting blood easily. In addition, as described above, it is not necessary to position a member having a guide function on a finger or the like before the blood collection and to bring a lancet close to the finger after recognizing the member. Therefore, the operation can be carried out more easily and quickly. Furthermore, since the blood-collection position indicator can be fixed to the skin without using such a band as described above, the blood collection site is not limited. Consequently, when the first blood-collection position indicator of the present invention is used, for example, even patients with visual handicap or the like can collect blood easily, and it also is possible to collect blood easily from a site such as an ear or the like, which is difficult to be recognized by the patient himself. Thus, the first blood-collection position indicator is useful for blood collection for diagnosis in clinical medicine and particularly for self-diagnosis at home.

The following examples are preferable as the configuration of the attachment part.

For instance, in the case of a blood-collection position indicator in which the blood collection hole serves as the attachment part, the tip of the lancet device may be inserted into the blood collection hole, thus attaching the blood-collection position indicator to the tip of the lancet device. In the case of a blood-collection position indicator having a protruding portion as the attachment part, the protruding portion may be inserted into a hole of the tip of the lancet device, thus attaching the blood-collection position indicator to the tip of the lancet device. In addition, in the case of a blood-collection position indicator having a cylindrical shape with a bottom, it is preferable that its inner space (hereinafter also referred to as a "concave portion") serves as the attachment part, the tip of a lancet device is inserted into the concave portion, thus attaching the blood-collection position indicator to the tip of the lancet device, the bottom is provided with a through hole serving as the blood collection hole, and an outer bottom face of the bottom is provided with the adhesive portion. In the specification, the "cylindrical shape" of the cylindrical shape with a bottom is not limited to one with a circular planar shape and may be one whose planar shape is rectangular, polygonal, or the like.

Preferably, an inner circumferential face of a cylindrical portion with the cylindrical shape with a bottom has at least one groove along a depth direction, a part of a peripheral surface of the tip of the lancet device is brought into contact with and is pressed against a portion except for the groove of the inner circumferential face, thus attaching the blood-collection position indicator to the tip of the lancet device in a pressure contact state, and the part being in contact with and being pressed against the portion is movable to be positioned in the groove, thus releasing the pressure contact state.

Preferably, the tip of the lancet device has a rectangular shape. It is preferable that the blood-collection position indicator has the following configuration. For example, the inner circumferential face of the cylindrical portion having the cylindrical shape with a bottom is provided with at least one groove along the depth direction, corners of the rectangular tip of the lancet device are brought into contact with and are pressed against the portion except for the groove of the inner circumferential face, thus attaching the blood-collection position indicator to the tip of the lancet device in a pressure contact state, and the corners of the rectangular tip are moved to be positioned in the groove, thus releasing the pressure contact state. Alternatively, according to another preferred embodiment, the tip of the lancet device has an elliptical shape. It is preferable that the blood-collection position indicator has the following configuration. For example, the inner circumferential face of the cylindrical portion having the cylindrical shape with a bottom is provided with at least one groove along the depth direction, side ends, in a major axis direction, of the elliptical tip of the lancet device are brought into contact with and are pressed against the portion except for the groove of the inner circumferential face, thus attaching the blood-collection position indicator to the tip of the lancet device in a pressure contact state, and the side ends being in contact with and being pressed against the portion are moved to be positioned in the groove, thus releasing the pressure contact state.

Preferably, the blood collection hole includes a portion with a tapered shape expanding in a direction away from the skin, in use. Thus, in the case of a blood-collection position indicator having a cylindrical shape with a bottom, it is preferable that the through hole includes a portion with a tapered shape expanding toward an inner portion of the cylindrical portion. This allows blood to flow easily into the concave portion of the cylindrical shape with a bottom.

As described above, the first blood-collection position indicator may be attached to the tip of the lancet device to form one body through the above-mentioned insertion. A surface to be brought into contact with the tip of the lancet device may, for example, be provided with an adhesive portion serving as the attachment part, and the blood-collection position indicator may be attached to the tip of the lancet device by adhesion through the adhesive portion.

Preferably, an annular protruding portion surrounding the blood collection hole is provided on a surface to be positioned to face the skin. The formation of such an annular protruding portion prevents blood from flowing through a gap between the skin and the blood-collection position indicator by a capillary phenomenon. This also prevents blood to be collected from leaking out from the blood-collection position indicator. For instance, even when a double-sided tape or the like is used for the adhesive portion to allow the blood-collection position indicator to adhere to the skin, problems such that its adhesive strength is decreased due to the penetration of blood into the double-sided tape or the like are not caused in a considerable manner.

Preferably, the blood collection hole has a quantitative function. It has been difficult for a patient to judge whether the amount of collected blood is a sufficient amount required for measurement when the patient collects blood by himself. According to this, however, a sufficient or certain amount of blood can be collected easily. The quantitative function can be obtained, for example, by setting of the internal volume of the blood collection hole according to the amount of blood required for the measurement or the like. However, it is preferred to set the internal volume of the blood collection hole with consideration to factors such as surface tension and viscosity of blood.

Preferably, the first blood-collection position indicator further includes a cover layer on a surface of the adhesive portion, to be stuck to the skin, wherein the cover layer is removable before the adhesive portion is stuck to the skin. Such a cover layer can prevent the deterioration in adhesiveness.

As described above, it is preferable that the first blood-collection position indicator of the present invention has a cylindrical shape with a bottom. More preferably, the first blood-collection position indicator has the following configuration. A through hole serving as a blood collection hole is formed in the bottom of the cylindrical body with a bottom. An adhesive portion is provided on the outer bottom surface of the bottom. An annular protruding portion surrounding the through hole may be provided on the outer bottom surface. The through hole may include a portion with a tapered shape expanding toward the inner portion of the cylindrical body. The inner circumferential face of the cylindrical portion having the cylindrical shape with a bottom may be provided with at least one groove. A part of the peripheral surface of the tip of a lancet device may be brought into contact with and pressed against a portion except for the groove of the inner circumferential face, thus attaching the first blood-collection position indicator to the tip of the lancet device in a pressure contact state, and the part being in contact with and being pressed against the portion may be moved to be positioned in the groove, thus releasing the pressure contact state.

A second blood-collection position indicator of the present invention includes a pair of clip members, wherein the pair of clip members are in contact with each other at a supporting point and include clip parts for holding skin, which are formed on one side with respect to the supporting point as the center, and grip parts formed on the other side, respectively, the clip parts are urged to be in a closed state, at least one of the clip parts has an attachment part to be attached to a tip of a lancet device including a lancet, and the attachment part is provided with a blood collection hole, through which the lancet can pass.

In such a second blood-collection position indicator of the present invention, as described above, since the clip parts are urged to be in a closed state (i.e. with the clip parts being pressed against each other when the clip is not in use), it is only necessary to hold a blood collection site such as a fingertip or the like with the clip parts using a force applied to the clip parts. Consequently, a patient can attach or detach the blood-collection position indicator easily. When an indicator is fixed to the blood collection site and, for example, an adhesive tape or the like is used, there is a fear of insufficient fixation due to the decrease or deterioration in adhesiveness or the like or a problem of cost increase for reusing it. However, since the second blood-collection position indicator of the present invention is fixed to the blood collection site sufficiently by the force applied to the clip parts, for example, even when the tip of a lancet device is attached to the blood-collection position indicator or skin is punctured by the lancet, it is avoided that the blood-collection position indicator is displaced or detached from the blood collection site due to such operations. When being reused, the second blood-collection position indicator of the present invention is required only to be washed, pasteurized, or the like, thus allowing cost reduction. In addition, it is easy for a patient to recognize the puncture site on the skin through the blood-collection position indicator using the sense of touch without relying on the visual sense or to collect blood by bringing the tip of a strip of the above-mentioned measuring instrument into contact with the blood pooled in the blood collection hole. Therefore, in the case of using the second blood-collection position indicator of the present invention, for example, it can be fixed to the blood collection site sufficiently and it is possible even for a patient with visual handicap or the like to collect blood easily. Thus, the second blood-collection position indicator of the present invention is useful for blood collection for diagnosis in clinical medicine, particularly for self-diagnosis at home.

Preferably, at least one of the clip parts is provided with a concave portion having a bottom, the bottom of the concave portion is provided with a through hole serving as the blood collection hole, and the tip of the lancet device is attached to an inner space of the concave portion. In such a blood-collection position indicator, for example, the tip of the lancet device may be inserted into the inner space, thus attaching the blood-collection position indicator to the tip of the lancet device, and then puncture and blood collection may be operated through the through hole. In this way, by providing the concave portion, the blood collection site is recognized easily by a patient and, for example, the tip of the lancet device or the tip of the strip of the aforementioned measuring instrument is brought into contact with blood in the blood-collection position indicator easily.

Preferably, the clip part having the blood collection hole is provided with an annular protruding portion surrounding the blood collection hole on a surface, of the clip part, to be brought into contact with the skin. The formation of such an annular protruding portion on the surface to be brought into contact with the skin can prevent blood from flowing through a gap between the skin and the blood-collection position indicator by a capillary phenomenon, thus allowing blood collection without wasting the blood. In addition, the annular protruding portion presses the skin to cause blood congestion, and therefore a sufficient amount of blood can be obtained easily.

Preferably, the blood collection hole has a quantitative function. It has been difficult for a patient to judge whether the amount of collected blood is a sufficient amount required for measurement when the patient collects blood by himself According to this, however, a sufficient or certain amount of blood can be collected easily. The quantitative function can be obtained, for example, by setting of the internal volume of the blood collection hole according to the amount of blood required for the measurement or the like. However, it is preferred to set the internal volume of the blood collection hole with consideration to factors such as surface tension and viscosity of blood.

Preferably, the attachment part can be detached. According to such a configuration, for example, when the second blood-collection position indicator is reused, only this attachment part may be washed, pasteurized, or the like, or alternatively, when the second blood-collection position indicator is a disposable type, only the attachment part may be replaced, thus achieving cost reduction. Therefore, the second blood-collection position indicator is useful particularly for blood collection at home or the like.

In the second blood-collection position indicator of the present invention, the following examples are preferable as the configuration of the attachment part and the attachment state between the tip of the lancet device and the attachment part.

Preferably, the concave portion has an inner circumferential face provided with at least one groove along a depth direction, a part of the peripheral surface of the tip of the lancet device is brought into contact with and is pressed against a portion except for the groove of the inner circumferential face, thus attaching the attachment part to the tip of the lancet device in a pressure contact state, and the part being in contact with and being pressed against the portion is movable to be positioned in the groove, thus releasing the pressure contact state.

Preferably, the tip of the lancet device has a rectangular shape and corners of the tip are brought into contact with and are pressed against the portion except for the groove of the inner circumferential face of the concave portion, thus attaching the attachment part to the tip of the lancet device in a pressure contact state, and the corners are moved to be positioned in the groove, thus releasing the pressure contact state. Alternatively, according to another embodiment, the tip of the lancet device has an elliptical shape and side ends of the tip in a major axis direction are brought into contact with and are pressed against the portion except for the groove of the inner circumferential face of the concave portion, thus attaching the attachment part to the tip of the lancet device in a pressure contact state, and the side ends being in contact with and being pressed against the portion are moved to be positioned in the groove, thus releasing the pressure contact state.

Preferably, the blood collection hole includes a portion with a tapered shape expanding in a direction away from the skin, in use. This allows blood to flow easily into the inner space of the concave portion.

BRIEF DESCRIPTION OF THE DRAWINGS

FIGS. 26A and 26B show a further embodiment of the second blood-collection position indicator according to the present invention, wherein FIG. 26A is a perspective view of a main body and FIG. 26B is a perspective view of an attachment member to be attached to the main body.

DETAILED DESCRIPTION OF THE INVENTION

Examples of the first blood-collection position indicator according to the present invention are described in the following embodiments A-1 to A-12.

Embodiment A-1

Figure 1A:
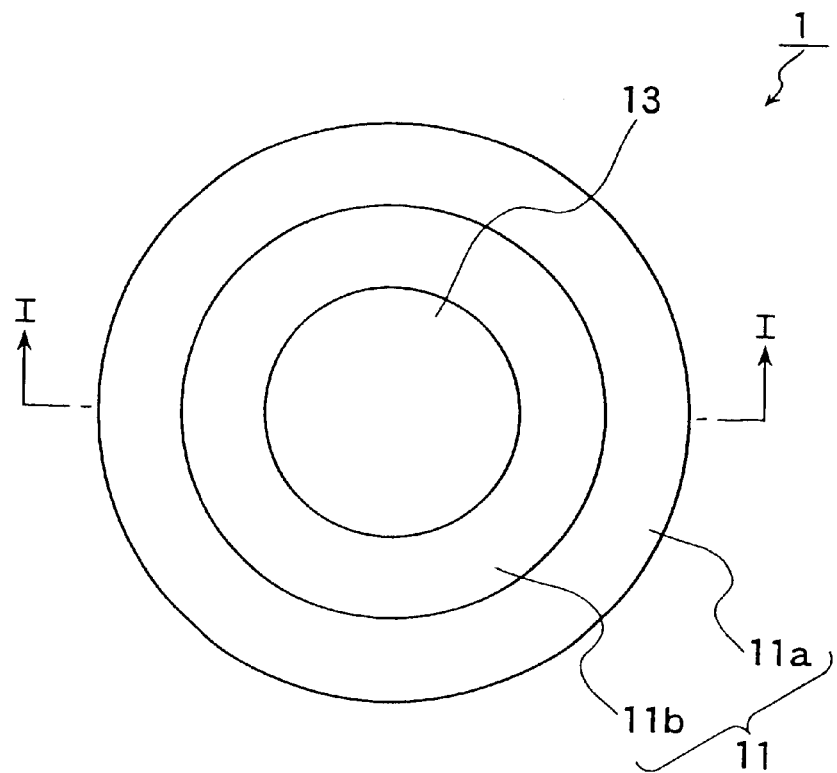
FIG. 1A is a plan view showing an embodiment of the first blood-collection position indicator according to the present invention and FIG. 1B is a sectional view thereof.
Figure 1B:
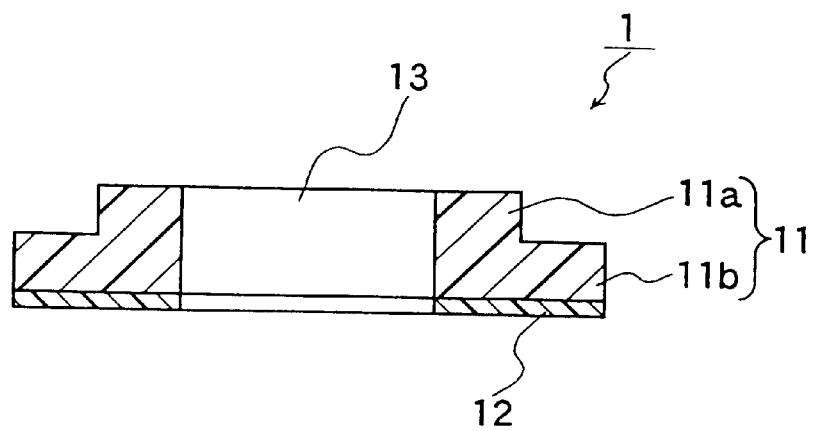

FIGS. 1A and 1B show an example of the first blood-collection position indicator according to the present invention. FIG. 1A is a plan view of this blood-collection position indicator, and FIG. 1B is its sectional view taken in the I—I direction in the plan view. As shown in the figures, this blood-collection position indicator 1 includes a base 11 and an adhesive layer 12 formed on its bottom face and has a circular planar shape and a convex cross-section. This blood-collection position indicator 1 has, at its center, a through hole passing through the base 11 and the adhesive layer 12, which serves as a blood collection hole 13. The base 11 includes a substrate portion 11b and a protruding portion 11a. The protruding portion 11a serves as an attachment part to be attached to the tip of a lancet device.

The material of the base 11 is not particularly limited. Examples of the material include plastics such as polystyrene, polyester, polycarbonate, polypropylene or the like, metal such as aluminum, stainless steel, or the like, rubber, vinyl chloride, or the like.

Examples of the material that can be used for the adhesive layer 12 include glues for medical applications, adhesives for medical applications such as an acrylic adhesive or the like, double-sided tapes, or the like. For instance, the adhesive layer 12 can be formed through application of the adhesive to or attachment of the double-sided tape to the bottom face of the base 11. In this case, as described above, it is required to set the adhesive strength of the adhesive layer 12 to the skin to be stronger than the attachment strength of the attachment part to the tip of a lancet device. In order to prevent deterioration in adhesiveness, it is preferred to laminate a cover layer on the bottom face of the adhesive layer 12. The cover layer can be removed before the adhesion of the adhesive layer 12 to the skin. As the cover layer, for example, a plastic film made of a polyurethane film, a resin-coated paper, or the like or a peeling paper can be used.

Figure 2:
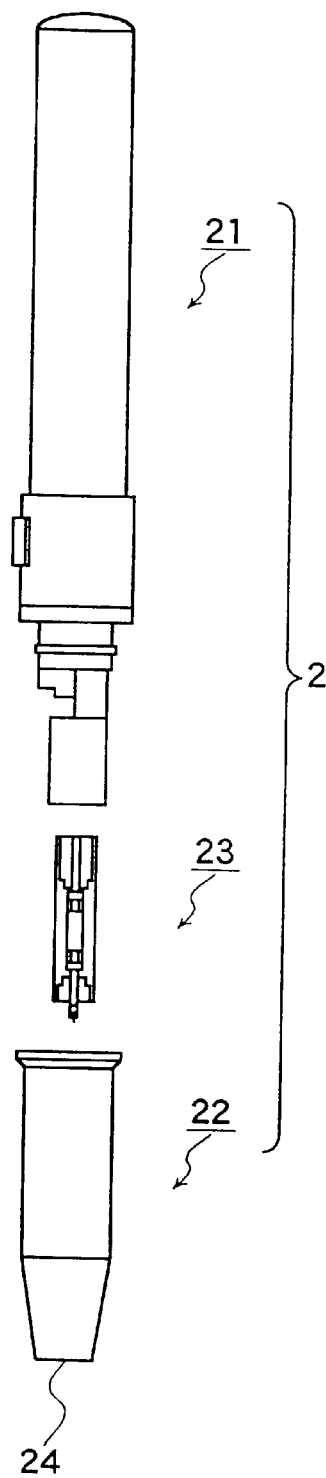
FIG. 2 is a schematic view showing a structural example of a lancet device and a lancet.

Such a blood-collection position indicator 1 can be used together with, for example, a lancet and a lancet device as shown in FIG. 2 as follows.

As shown in the figure, a lancet device 2 includes a main body 21 in which a disposable lancet 23 such as a needle or a cutting tool is set, and a hollow leading-end member 22. When the lancet device 2 is used, the lancet 23 is attached to the main body 21 and the leading-end member 22 is attached to the main body 21 so that the lancet 23 is covered. In the main body 21, an elastic body is provided for ejecting the lancet 23 set therein and restoring it to the original position immediately after the ejection. An end face 24 of the leading-end member 22 is provided with a hole for puncture at its center so that the lancet 23 set inside the main body 21 can be ejected to puncture the skin.

As the lancet device 2, for example, one that is commercially available can be used. The size of the lancet device 2 is not particularly limited, but for example, its a maximum overall length is in the range between 3 and 15 cm, its maximum diameter in the range between 10 and 20 mm, the diameter of the end face 24 in the range between 3 and 20 mm, and a diameter of the hole for puncture in the range between 0.5 and 5 mm. Furthermore, the shape of the lancet device 2 is not limited to a cylindrical form.

Figure 3:
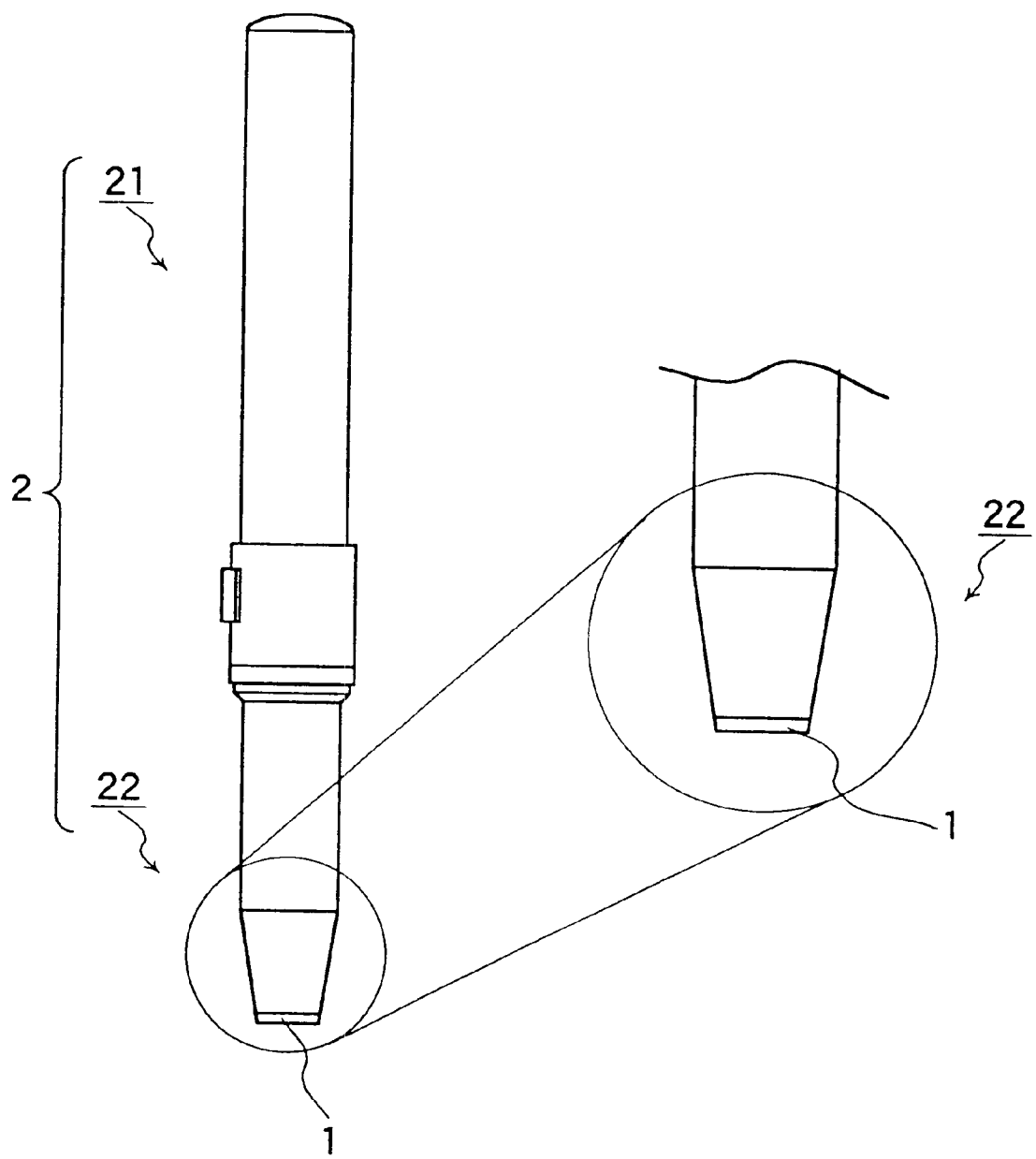
FIG. 3 is a schematic view showing a state where the blood-collection position indicator of the embodiment is inserted into the tip of the lancet device.

After the lancet device 2 is thus set, as shown in FIG. 3, the protruding portion 11a is inserted into the hole for puncture of the leading-end member 22, thus attaching the blood-collection position indicator 1 to the leading-end member 22. In FIG. 3, the same parts as those in FIG. 2 are indicated with the same numerals. When the lancet device 2 with the size described above is used, as the size of the blood-collection position indicator 1, for example, the height of the protruding portion 11a is in the range between 0.1 and 5 mm, the thickness of the substrate portion 11b in the range between 0.1 and 5 mm, the diameter of the substrate portion 11b in the range between 5 and 20 mm, the diameter of the blood collection hole 13 in the range between 0.5 and 8 mm, the diameter of the protruding portion 11a in the range between 5 and 20 mm, and the thickness of the adhesive layer 12 in the range between 0.01 and 3 mm.

Figure 4A:
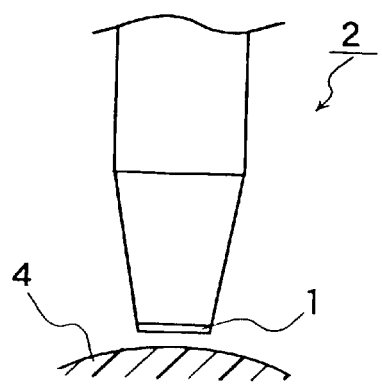
FIG. 4A is a schematic view showing a state where the lancet device with the blood-collection position indicator of the embodiment being attached thereto is brought close to the skin.
Figure 4B:
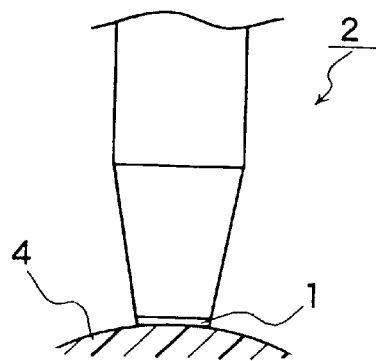
FIG. 4B is a schematic view showing a state where the blood-collection position indicator is allowed to adhere to the skin.
Figure 4C:
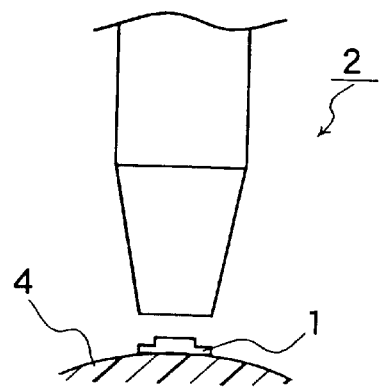
FIG. 4C is a schematic view showing a state where only the blood-collection position indicator remains on the skin after puncture.
Figure 5:
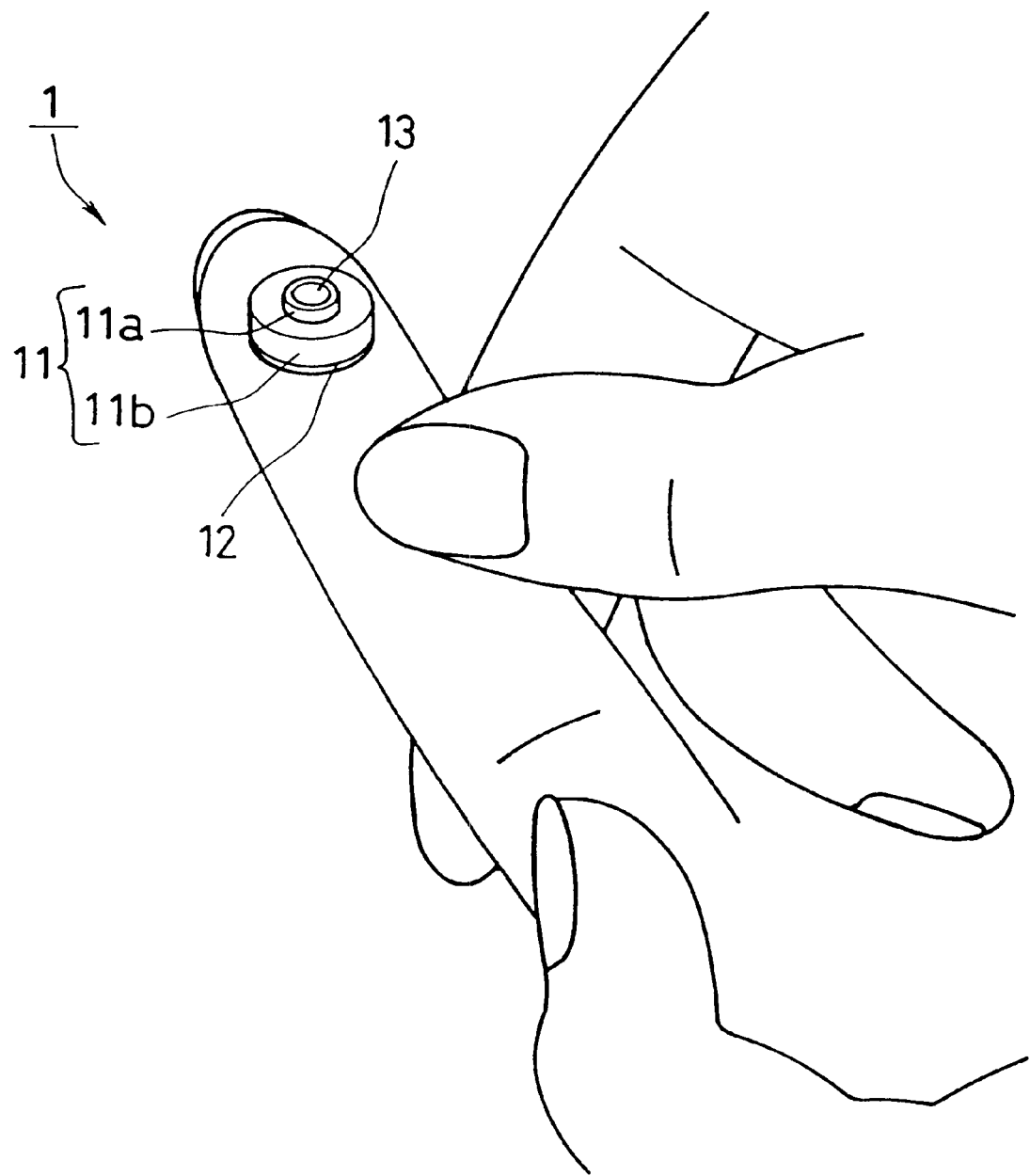
FIG. 5 is a schematic view showing a state where the blood-collection position indicator of the embodiment remains on the skin.

As shown in FIG. 4A, the lancet device 2 provided with the blood-collection position indicator 1 is brought close to the skin 4 and the position to be punctured is determined. After that, the lancet device 2 is pressed against the skin 4 as shown in FIG. 4B. This allows the blood-collection position indicator 1 to adhere to the skin 4 through the adhesive layer, and thus the lancet device 2 is fixed via the blood-collection position indicator 1. Then the lancet is ejected from the lancet device 2 to puncture the skin 4. After that, when the lancet device 2 is moved away from the skin 4, only the blood-collection position indicator 1 remains on the skin 4 as shown in FIG. 4C and FIG. 5. In FIG. 5, the same parts as those in FIG. 1 are indicated with the same numerals and characters.

By the puncture described above, blood is collected inside the blood collection hole 13 of the blood-collection position indicator 1 adhering to the skin. As shown in FIG. 5, more blood may be allowed to bleed by squeezing of the finger as required.

It also is possible to provide quantitativity by, for example, setting the size of the blood collection hole 13 (the height of the protruding portion 11a, the height of the substrate portion 11b, the diameter of the blood collection hole 13, and the like). For instance, when blood in the range between 3 and 10 μl is to be collected, it is preferred to set the size of the blood collection hole 13 so that its volume is in the range between $3 \times 10^{-3}$ and 0.01 cm$^3$, the height of the protruding portion 11a in the range between 0.3 and 0.8 mm, the height of the substrate portion 11b in the range between 0.2 and 0.7 mm, and the diameter in the range between 2.8 and 3.6 mm.

Figure 6:
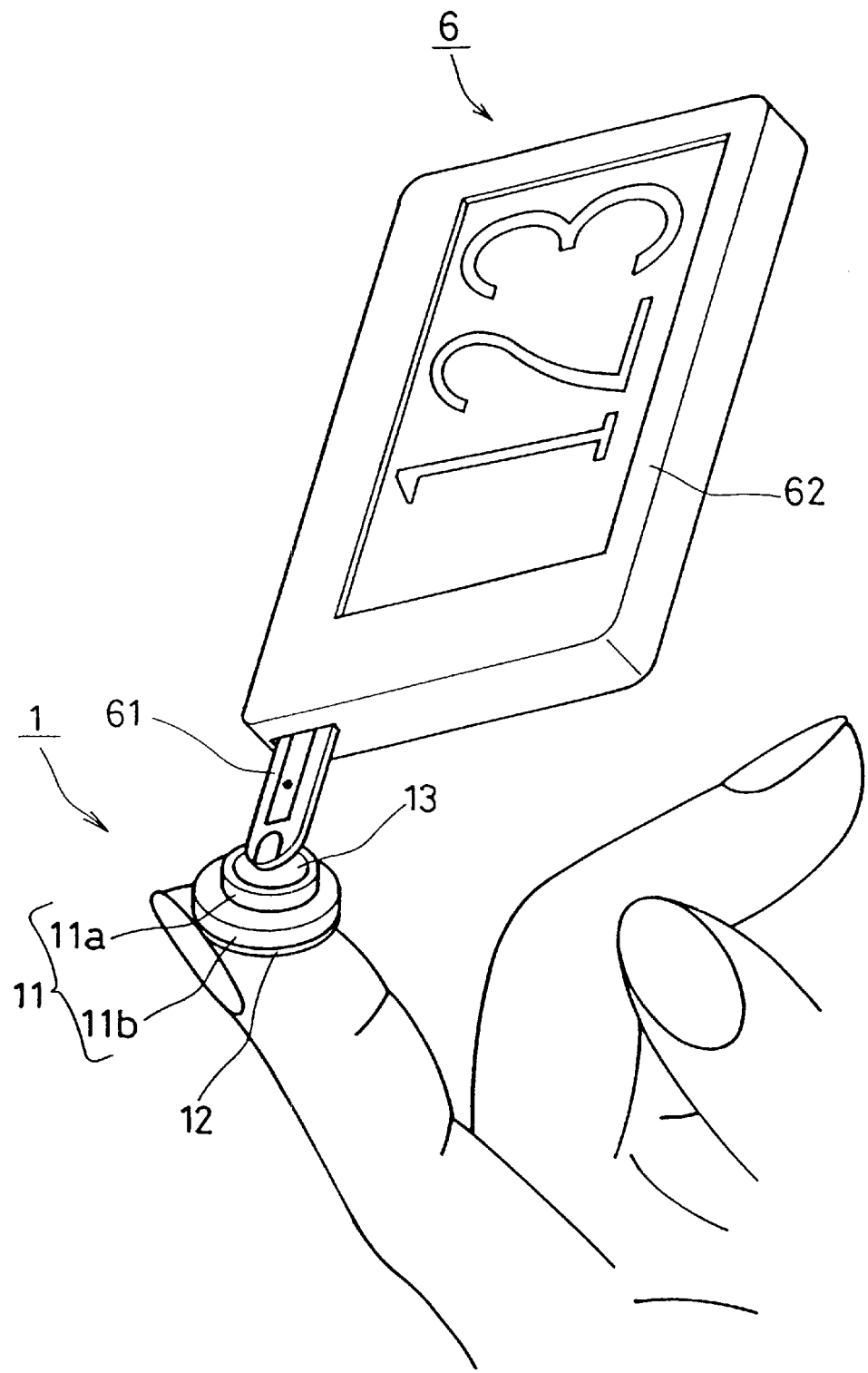
FIG. 6 is a schematic view showing a state where blood is collected from a blood collection hole of the blood-collection position indicator of the embodiment.
Figure 23:
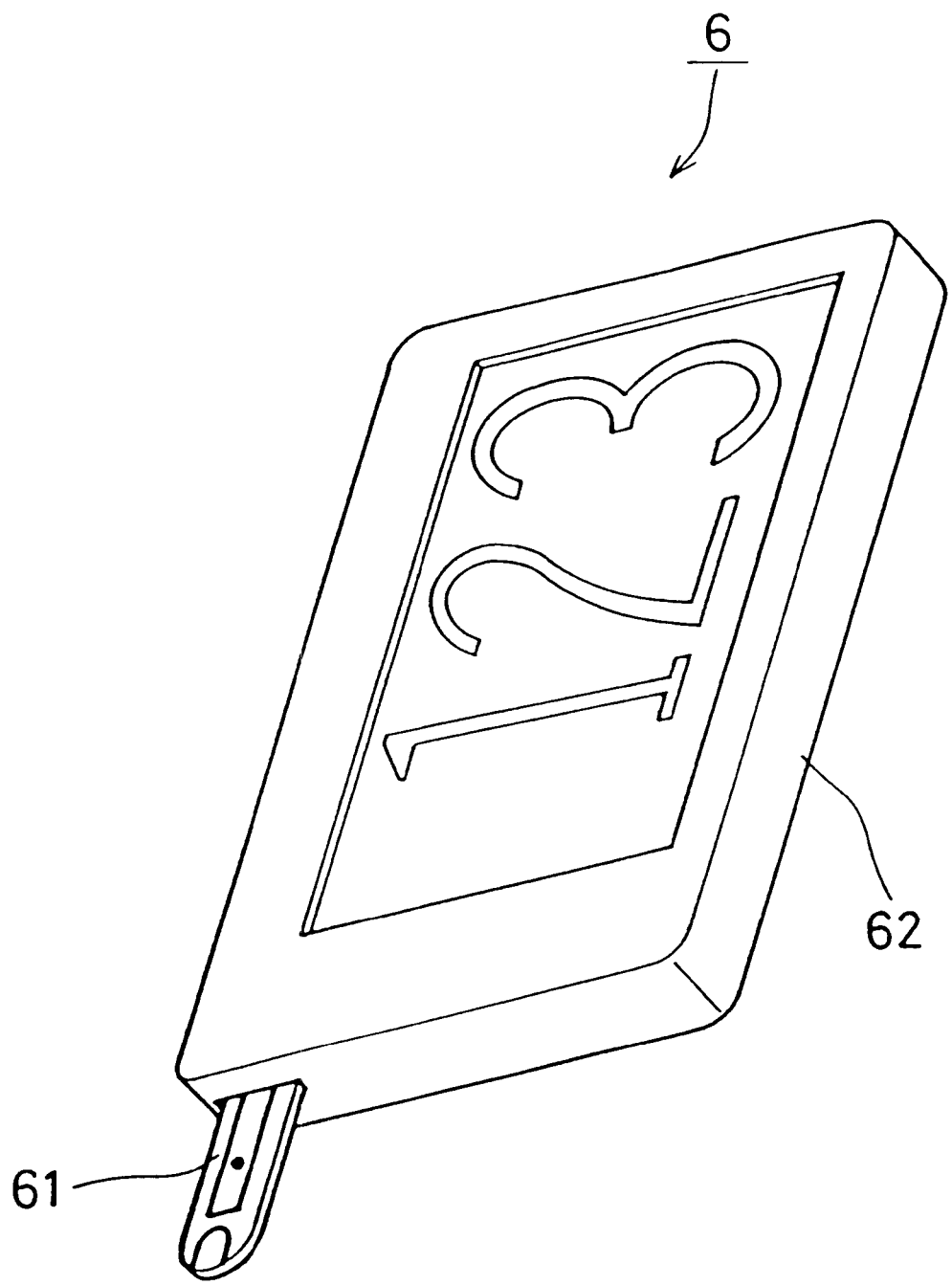
FIG. 23 is a perspective view showing an example of a simplified glucose measuring instrument.

When a glucose content is measured using such a measuring instrument (see FIG. 23) as described above, a patient recognizes the blood-collection position indicator 1 and brings the tip of a strip 61 of the measuring instrument 6 into contact with the blood collection hole 13 to allow blood to be absorbed by a capillary phenomenon as shown in FIG. 6. The blood is transported inside the strip 61, and in a reagent part, a reagent and glucose in the blood react with each other. After both are reacted with each other for a certain period, the meter 62 of the measuring instrument 6 detects the reactant of them automatically and computes it into a glucose concentration, which then is displayed on a monitor. In FIG. 6, the same parts as those in FIG. 1 are indicated with the same numerals and characters.

Embodiment A-2

Figure 7:
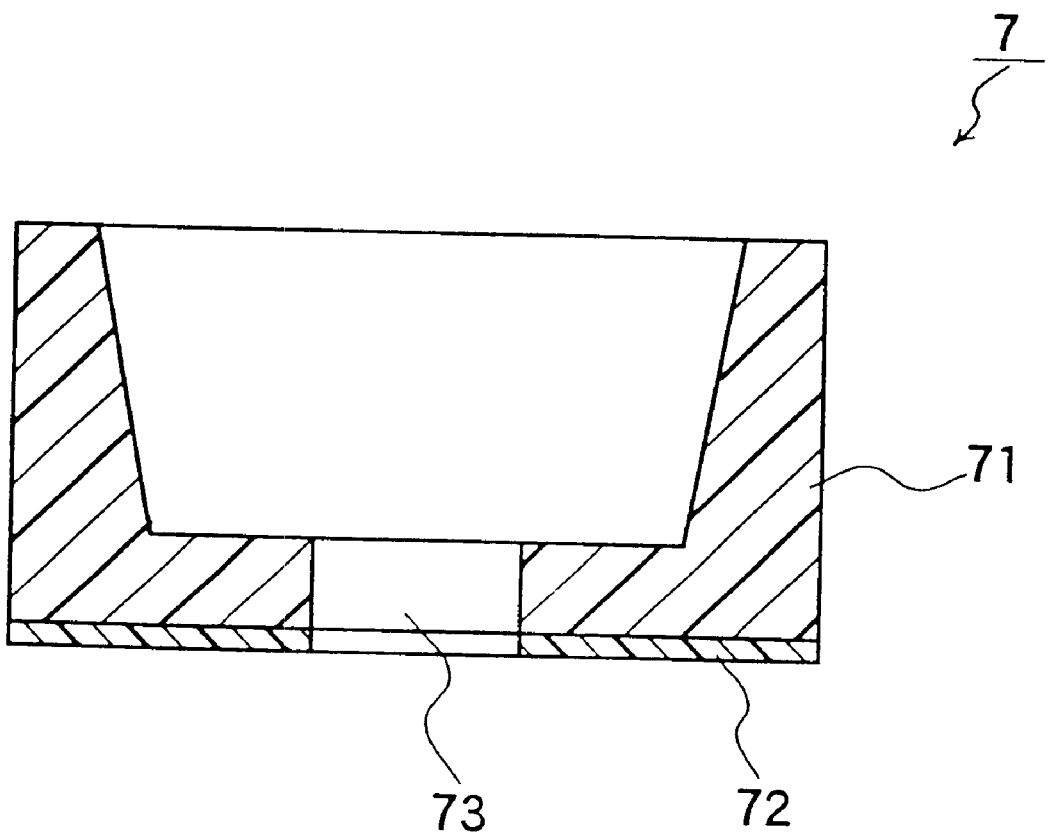
FIG. 7 is a sectional view showing another embodiment of the first blood-collection position indicator according to the present invention.

In a sectional view shown in FIG. 7, another example of the first blood-collection position indicator according to the present invention is illustrated. As shown in the figure, this blood-collection position indicator 7 includes a base 71 having a cylindrical shape with a bottom (a concave cross-section) and an adhesive layer 72 positioned on the back face of the bottom. A through hole 73 passing through the base 71 and the adhesive layer 72 is provided. In the blood-collection position indicator 7, the tip of a lancet device is inserted into the concave portion, thus attaching the blood-collection position indicator 7 to the tip. The inner circumferential face of the blood-collection position indicator 7 is a tapered face expanding toward an opening. The through hole 73 serves as a blood collection hole, through which blood passes to be pooled in the concave portion of the blood-collection position indicator 7. The method of using the blood-collection position indicator 7 is the same as in the embodiment A-1 except that the method of attaching it to the tip of the lancet device is different.

Embodiment A-3

Figure 8A:
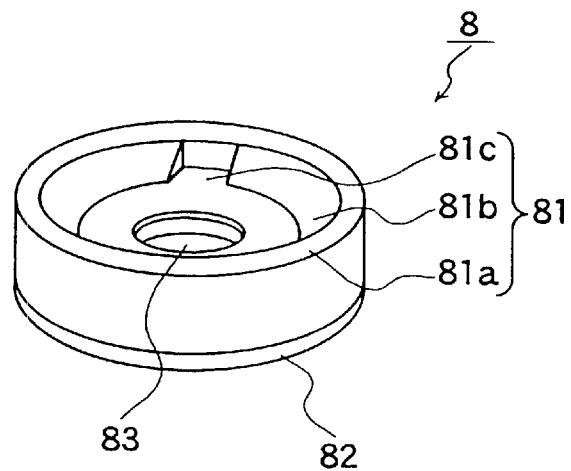
FIG. 8A is a perspective view showing a further embodiment of the first blood-collection position indicator according to the present invention.
Figure 8B:
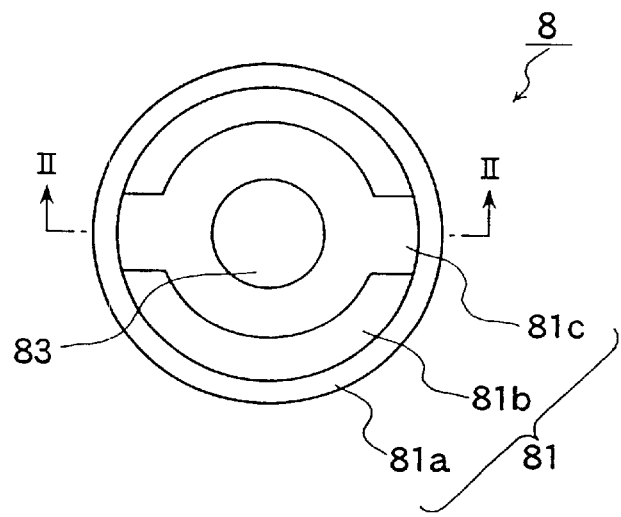
FIG. 8B is a plan view thereof.
Figure 8C:
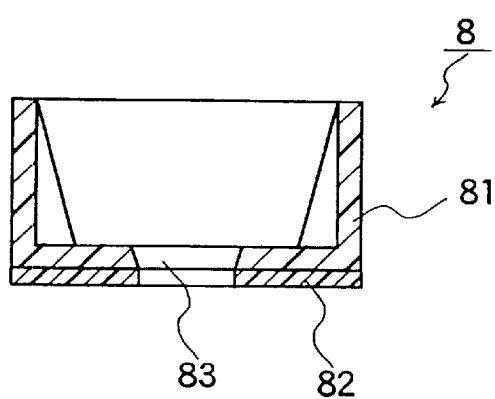
FIG. 8C is a sectional view thereof.

FIGS. 8A to 8C show an example of a blood-collection position indicator that can be applied to both lancet devices with circular and rectangular tips. FIG. 8A is a perspective view of this blood-collection position indicator 8, FIG. 8B is a plan view thereof, and FIG. 8C is a sectional view taken in the II—II direction in the plan view. As shown in the figures, the blood-collection position indicator 8 includes a base 81 having a cylindrical shape with a bottom (a concave portion) and an adhesive layer 82 positioned on the back face of the bottom. A through hole (a blood collection hole) 83 passing through the base 81 and the adhesive layer 82 is provided. The inner circumferential face of the base 81 is a tapered face 81b expanding toward an opening and has two cut portions 81c. In the figures, numeral 81a indicates a cylindrical portion of the base 81.

Figure 9:
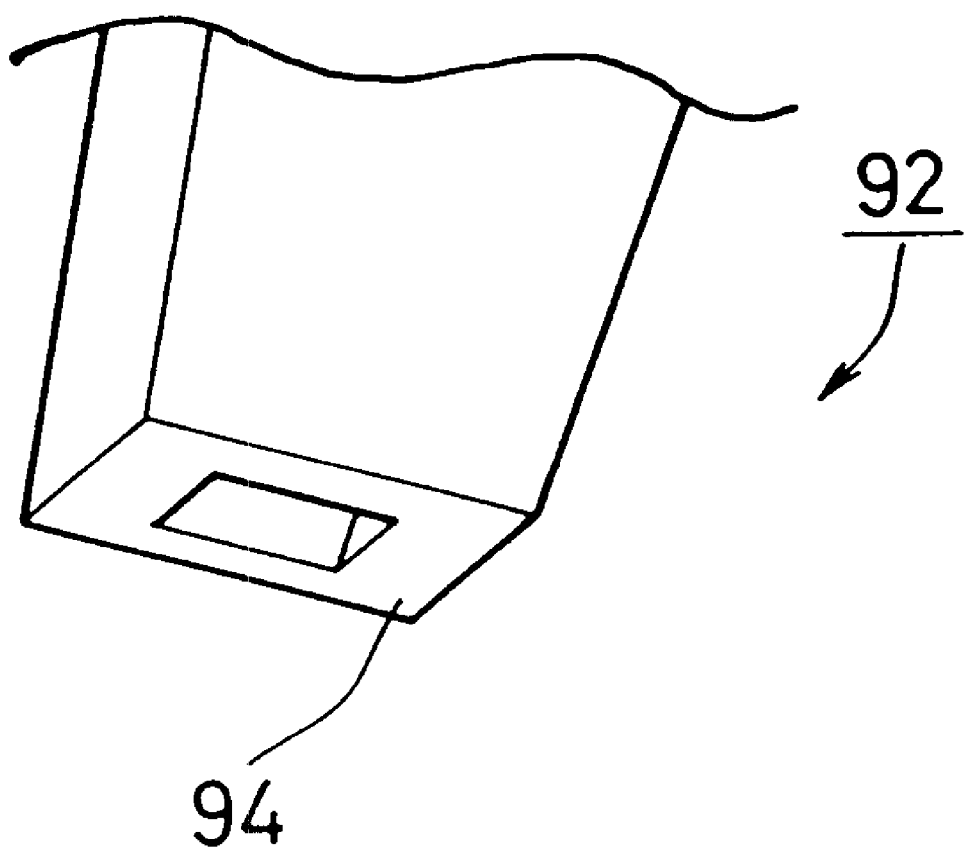
FIG. 9 is a perspective view showing another example of the lancet device.

When such a blood-collection position indicator 8 is applied, for example, to a leading-end member 92 of a lancet device with a rectangular end face 94 as shown in FIG. 9, the leading-end member 92 is inserted into the cut portions 81c, thus attaching the blood-collection position indicator 8 to the tip of the lancet device. In the case of a lancet device with a round tip, it may be inserted into the whole concave portion of the blood-collection position indicator 8 as in the embodiment A-2. The other application methods are the same as in the embodiment A-1.

The following embodiments A-4 to A-7 show examples of the blood-collection position indicator useful for a lancet device with a tip having a convex shape.

Embodiment A-4

Figure 10A:
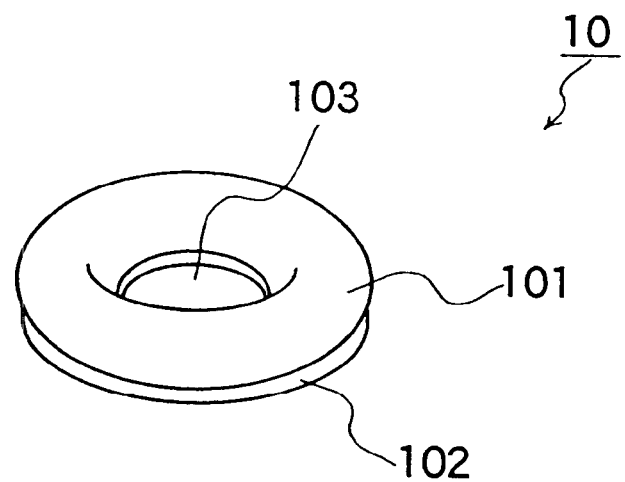
FIG. 10A is a perspective view showing still another embodiment of the first blood-collection position indicator according to the present invention.
Figure 10B:
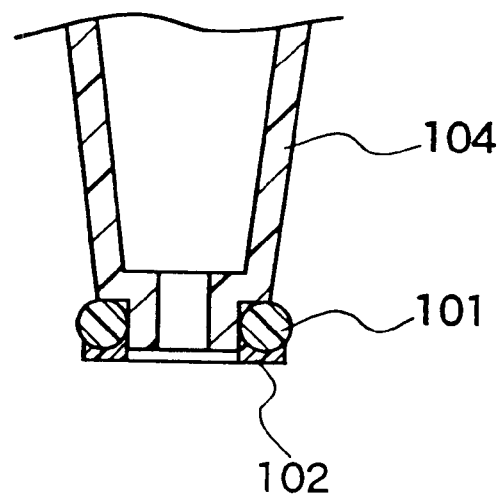
FIG. 10B is a sectional view showing a state where a lancet device is inserted into the blood-collection position indicator.

FIGS. 10A and 10B show an example of a ring-shaped blood-collection position indicator. FIG. 10A is a perspective view of this blood-collection position indicator and FIG. 10B is a sectional view showing a state where this blood-collection position indicator is attached to the tip of a lancet device.

As shown in the figures, this blood-collection position indicator 10 includes a ring-shaped base 101 with a circular cross-section and an adhesive layer 102 positioned on the back face of the base 101. A space surrounded by the ring portion serves as a blood collection hole 103.

As shown in FIG. 10B, the convex tip of a lancet device 104 is inserted into the blood collection hole 103, thus attaching the blood-collection position indicator 10 to the tip. The other application methods are the same as in the embodiment A-1.

Embodiment A-5

Figure 11A:
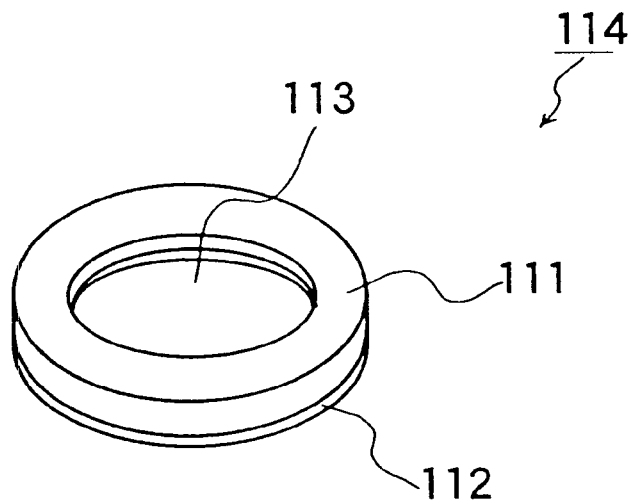
FIG. 11A is a perspective view showing yet another embodiment of the first blood-collection position indicator according to the present invention.
Figure 11B:
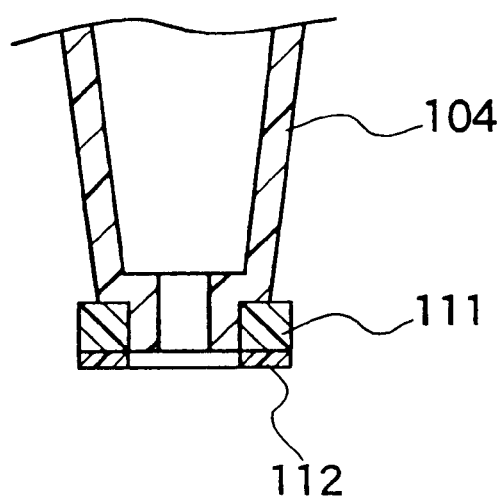
FIG. 11B is a sectional view showing a state where a lancet device is inserted into the blood-collection position indicator.

FIGS. 11A and 11B show another example of the ring-shaped blood-collection position indicator. FIG. 11A is a perspective view of this blood-collection position indicator and FIG. 11B is a sectional view showing a state where this blood-collection position indicator is attached to the tip of a lancet device.

As shown in the figures, this blood-collection position indicator 114 has the same configuration as that according to the embodiment A-4 except for having a square cross-section. As shown in FIG. 11B, the blood-collection position indicator 114 can be attached to the tip of the lancet device 104 as in the embodiment A-4. The other application methods are the same as in the embodiment A-1. In the figures, numeral 111 denotes a ring-shaped base of the blood-collection position indicator 114, numeral 112 indicates an adhesive layer, and the space surrounded by the ring-shaped base 111 is a blood collection hole 113.

Embodiment A-6

Figure 12A:
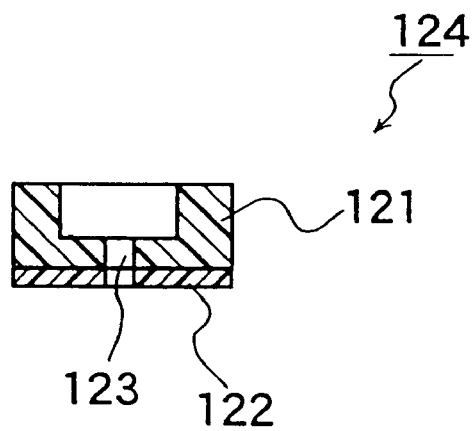
FIG. 12A is a sectional view of a further embodiment of the first blood-collection position indicator according to the present invention.
Figure 12B:
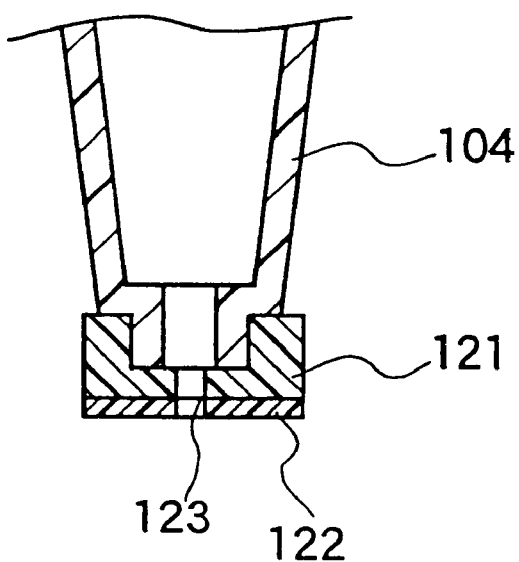
FIG. 12B is a sectional view showing a state where a lancet device is inserted into the blood-collection position indicator.

FIGS. 12A and 12B show another example of a blood-collection position indicator with a concave cross-section. FIG. 12A is a sectional view of this blood-collection position indicator and FIG. 12B is a sectional view showing a state where this blood-collection position indicator is attached to the tip of a lancet device.

As shown in the figures, this blood-collection position indicator 124 includes a base 121 having a cylindrical shape with a bottom (a concave shape) and an adhesive layer 122 positioned on the back face of the bottom. A through hole 123 passing through the base 121 and the adhesive layer 122 is provided and serves as a blood collection hole. In the blood-collection position indicator 124, the concave portion of the base 121 is a portion to be combined with a convex tip of the lancet device. The tip is inserted into the concave portion, thus attaching the blood-collection position indicator 124 to the tip. The other application methods are the same as in the embodiment A-1.

Embodiment A-7

Figure 13A:
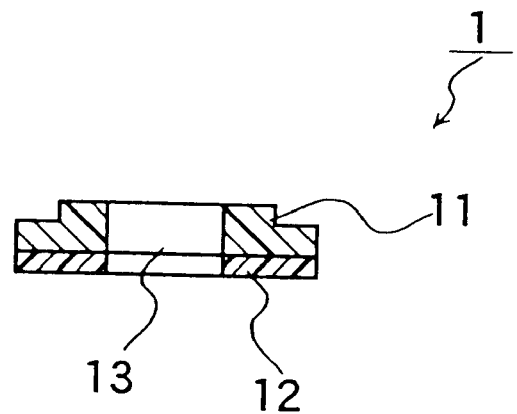
FIG. 13A is a sectional view of still another embodiment of the first blood-collection position indicator according to the present invention.
Figure 13B:
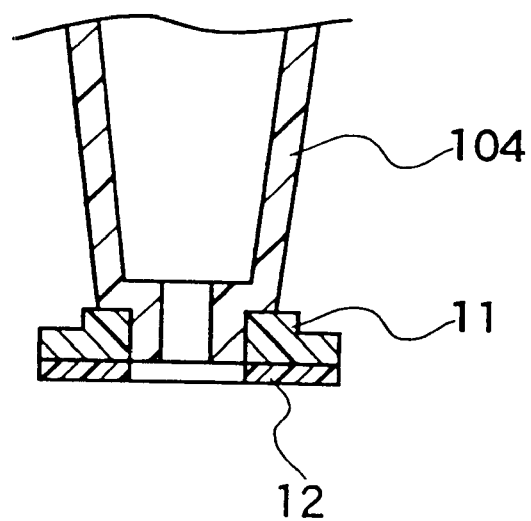
FIG. 13B is a sectional view showing a state where a lancet device is inserted into the blood-collection position indicator.

FIGS. 13A and 13B show another example of a blood-collection position indicator with a convex cross-section. FIG. 13A is a sectional view of this blood-collection position indicator and FIG. 13B is a sectional view showing a state where the blood-collection position indicator is attached to the tip of a lancet device. In the figures, the same parts as those in FIGS. 1A and 1B are indicated with the same numerals.

As shown in the figures, this blood-collection position indicator 1 has the same configuration as that of the blood-collection position indicator according to the embodiment A-1. In the present embodiment, however, a blood collection hole 13 serves as a portion to be combined with the lancet device, into which the convex tip of the lancet device 104 is inserted, thus attaching the blood-collection position indicator to the tip. The other application methods are the same as in the embodiment A-1 except that the method of attaching it to the tip of the lancet device is different.

Embodiment A-8

Figure 14:
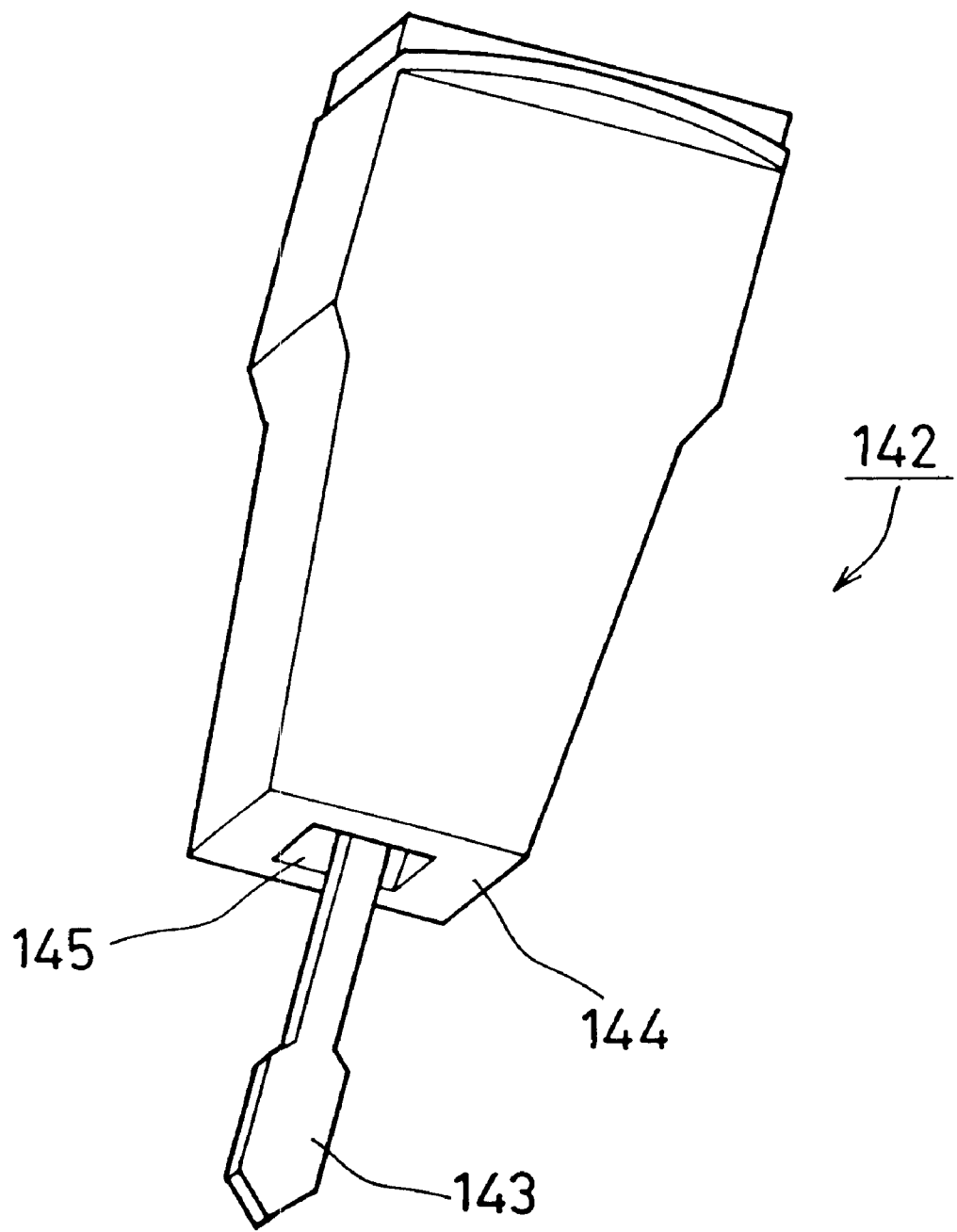
FIG. 14 is a perspective view showing a further example of the lancet device.

In this example, a blood-collection position indicator is applied to a lancet device with a lancet pre-attached to its leading-end member. This leading-end member is a disposable type. For instance, as shown in FIG. 14, the leading-end member 142 includes a lancet (not shown in the figure) preset in its inside and an end face 144 of the leading-end member 142 is provided with a puncture hole 145 for ejection of the lancet. To the lancet preset inside the leading-end member 142, a lancet cap 143 is attached. The end portion of the lancet cap 143 projects through the puncture hole 145.

Figure 15:
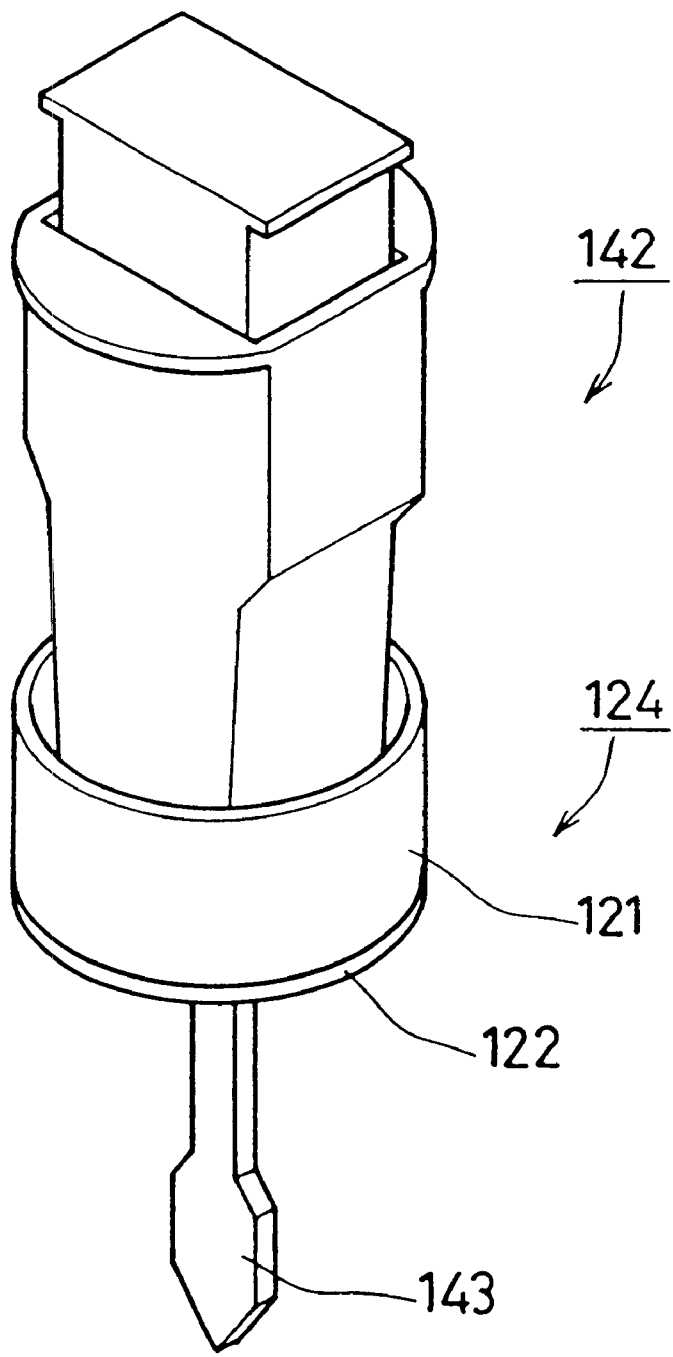
FIG. 15 is a perspective view showing a state where the lancet device is inserted into the first blood-collection position indicator according to yet another embodiment according to the present invention.

To such a leading-end member 142, for instance, the blood-collection position indicator with a concave cross-section (according to the embodiment A-6, see FIG. 12A) can be applied. As shown in FIG. 15, the lancet cap 143 is passed through the blood collection hole of the blood-collection position indicator 124 and then the leading-end member 142 is inserted into the concave portion of the blood-collection position indicator 124, thus attaching the blood-collection position indicator 124 to the lancet device. After the leading-end member 142 is attached to the main body of the lancet device, the lancet cap 143 is removed. Then, the end face of the blood-collection position indicator 124 is brought into contact with the skin and the lancet is ejected to puncture the skin. After the puncture, only the lancet device can be removed and blood can be collected as described above. In this case, the leading-end member 142 may be thrown away with the lancet cap 143 being attached to the used lancet again. In FIG. 15, the same parts as those in FIG. 12 are indicated with the same numerals.

Embodiment A-9

Figure 16:
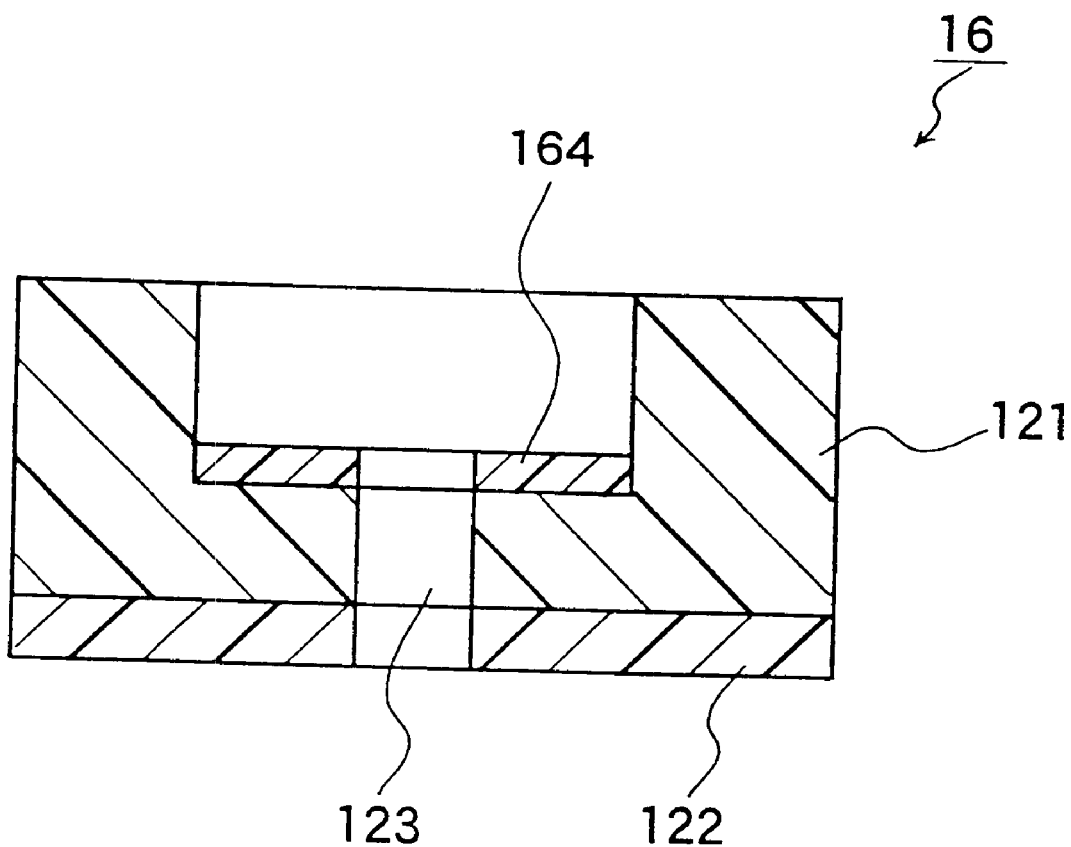
FIG. 16 is a sectional view showing still another embodiment of the first blood-collection position indicator according to the present invention.

The first blood-collection position indicator of the present invention may include an adhesive layer on a surface to be brought into contact with a lancet device. For instance, as in the blood-collection position indicator (see FIG. 12A) according to the embodiment A-6, in a blood-collection position indicator having a cylindrical shape with a bottom (a concave portion), when its concave portion serves as a portion to be combined with the tip of a lancet device, an adhesive layer 164 is formed on the bottom of the concave portion of the blood-collection position indicator 16 as shown in FIG. 16. This blood-collection position indicator 16 can be attached to the tip of the lancet device by adhesion via the adhesive layer 164. In FIG. 16, the same parts as those in FIG. 12 are indicated with the same numerals.

The material of the adhesive layer 122 is not particularly limited as long as the adhesive strength of the adhesive layer 122 to be brought into contact with the skin to the skin is stronger than that of the adhesive layer 164 to be brought into contact with the tip of the lancet device to the lancet device. Examples of their combination include a combination of a double-sided tape with high adhesiveness as the material of the adhesive layer 122 and a double-sided tape with low adhesiveness as the material of the adhesive layer 164. On the surfaces of the adhesive layers 122 and 164, cover layers as described above may be positioned.

Embodiment A-10

Figure 17A:
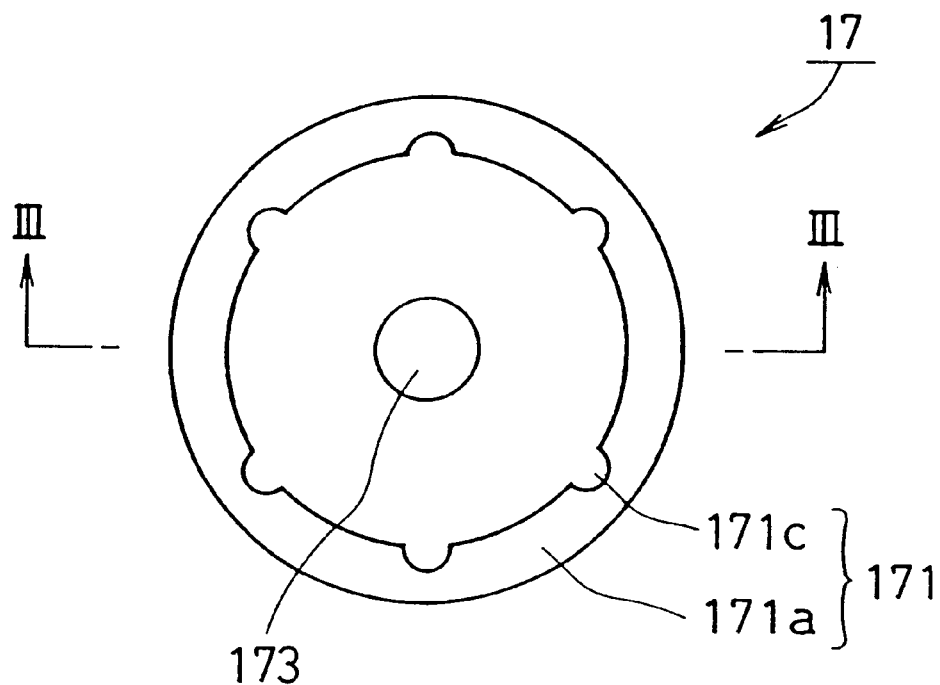
FIG. 17A is a plan view showing yet another embodiment of the first blood-collection position indicator according to the present invention.
Figure 17B:
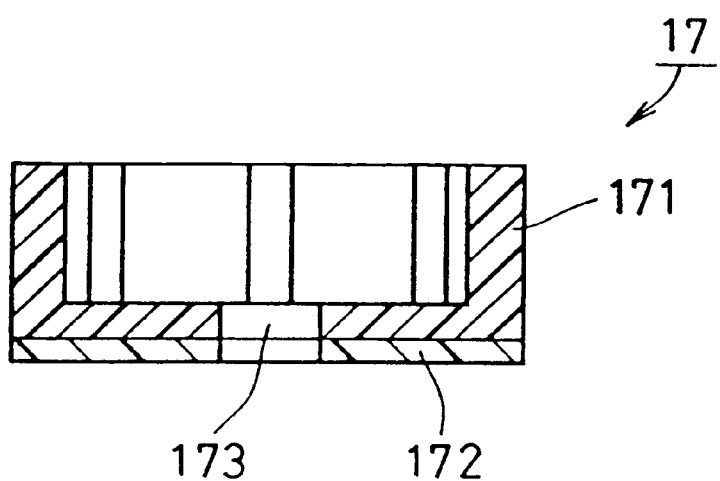
FIG. 17B is a sectional view thereof.

FIGS. 17A and 17B show an example of a blood-collection position indicator useful for a lancet device with a tip having a rectangular shape. FIG. 17A is a plan view of this blood-collection position indicator and FIG. 17B is a sectional view taken in the III—III direction in the plan view. As shown in the figures, the blood-collection position indicator 17 includes a base 171 having a cylindrical shape with a bottom and an adhesive layer 172 positioned on the back face of the bottom. A through hole (a blood collection hole) 173 passing through the base 171 and the adhesive layer 172 is provided. In the depth direction of the inner circumferential face of the base 171, six grooves 171c with a semicircular cross-section are equally spaced. In FIG. 17A, numeral 171a indicates a cylindrical portion of the base 171.

Figure 18A:
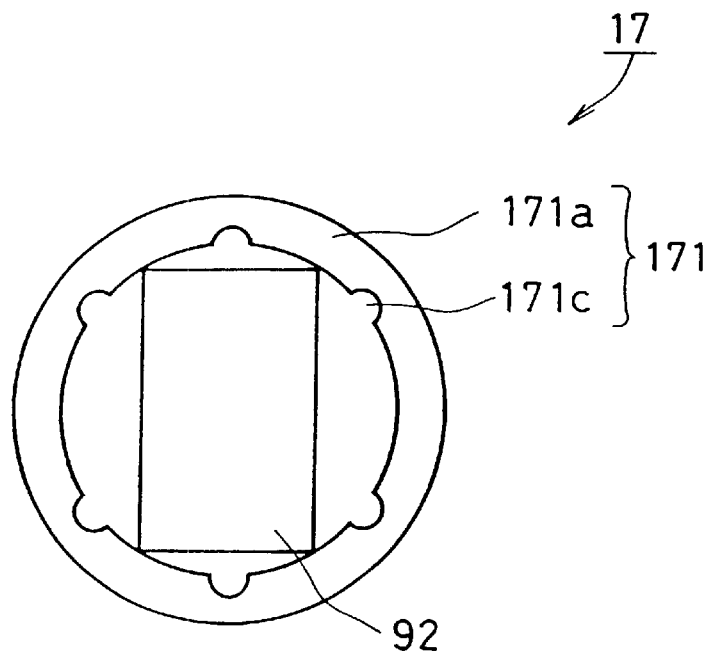
FIG. 18A is a plan view showing a state where the lancet device is brought into contact with and is pressed against the inner circumferential face of the blood-collection position indicator of the embodiment.
Figure 18B:
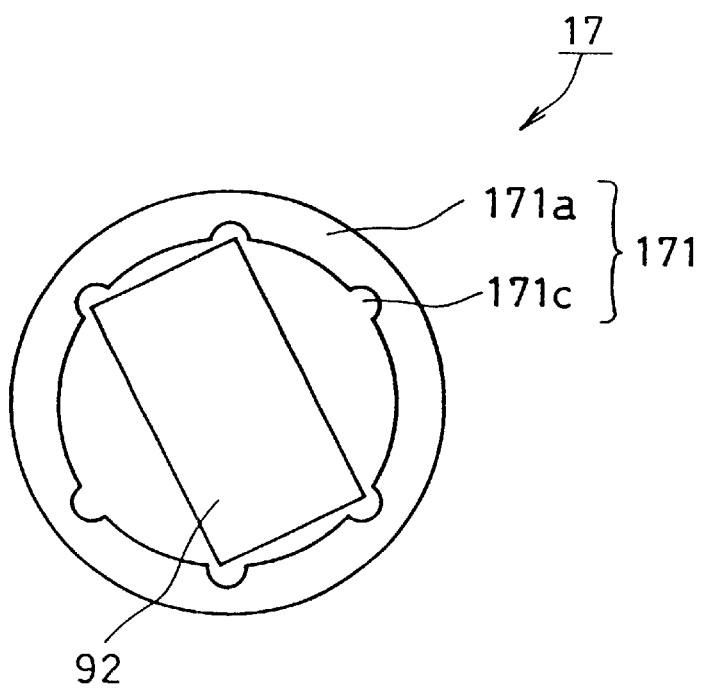
FIG. 18B is a plan view showing a state where the pressure contact state of the tip of the lancet device with the inner circumferential face of the blood-collection position indicator is released.

When such a blood-collection position indicator 17 is applied, for example, to the leading-end member 92 with a rectangular end face 94 (see FIG. 9) of the lancet device, as shown in FIG. 18A, the four corners of the leading-end member 92 are brought into contact with and are pressed against the inner circumferential face except for the grooves 171c of the base 171, thus attaching the blood-collection position indicator 17 to the tip of the lancet device. When the leading-end member 92 is to be detached from the blood-collection position indicator 17, as shown in FIG. 18B, the leading-end member 92 is rotated so that its four corners come to be positioned in the grooves 171c. When the four corners are positioned in the grooves 171c, the pressure contact state between the four corners and the inner circumferential face is released. Consequently, the leading-end member 92 can be detached easily. The other application methods are the same as in the embodiment A-1.

The number of the grooves are not particularly limited, but is for example, in the range between 1 and 12, preferably in the range between 3 and 12, more preferably in the range between 4 and 8, and particularly preferably 6. The positions of the grooves of the inner circumferential face can be determined suitably according to, for example, the shape of the tip of the leading-end member to be used or the like.

When the grooves are provided in a plurality of positions, the selection of the positions of the grooves, from those positions, corresponding to the shape of the tip of a leading-end member also enables the blood-collection position indicator 17 to be applied to leading-end members with various shapes. The shape of the grooves is not particularly limited, but preferably, the grooves have a cross-section of a circular arc shape, a V shape, a rectangular shape with its one side being open, or the like.

Embodiment A-11

Figure 19:
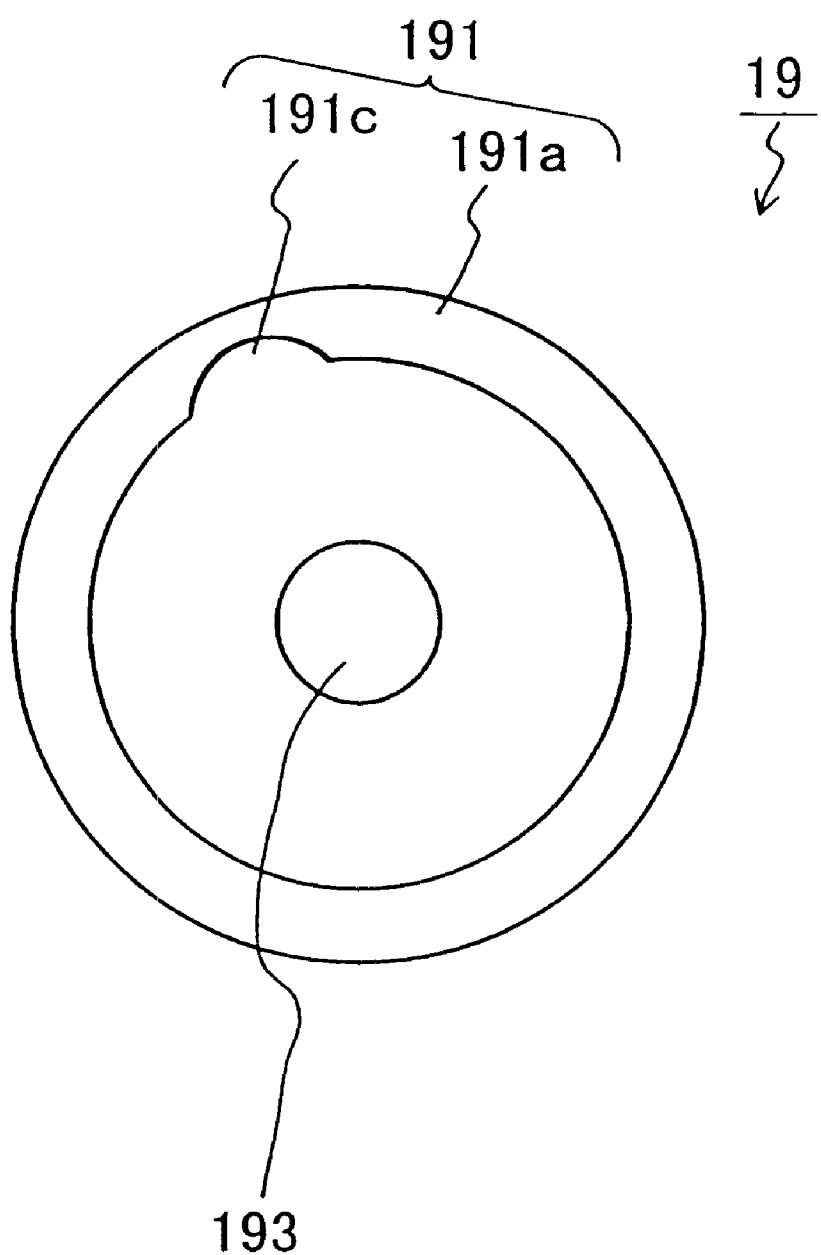
FIG. 19 is a plan view showing a further embodiment of the first blood-collection position indicator according to the present invention.

FIG. 19 shows an example of a blood-collection position indicator useful for a lancet device with a tip having an elliptical shape. FIG. 19 shows a plan view of the blood-collection position indicator 19. As shown in the figure, the blood-collection position indicator 19 includes a base 191 having a cylindrical shape with a bottom and an adhesive layer (not shown in the figure) positioned on the back face of the bottom. A through hole (a blood collection hole) 193 passing through the base 191 and the adhesive layer is provided. In the depth direction of the inner circumferential face of the base 191, a groove 191c with a semicircular cross-section is provided. In the figure, numeral 191a indicates a cylindrical portion of the base 191.

Figure 20A:
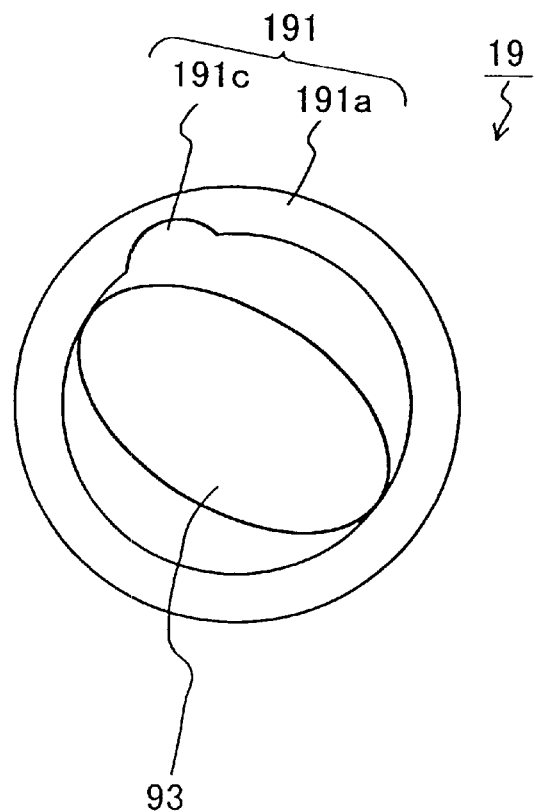
FIG. 20A is a plan view showing a state where the lancet device is brought into contact with and is pressed against the inner circumferential face of the blood-collection position indicator of the embodiment.
Figure 20B:
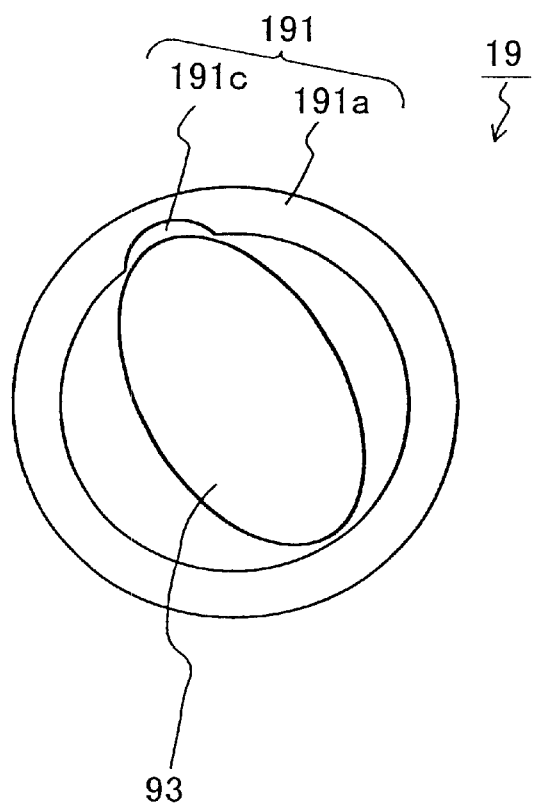
FIG. 20B is a plan view showing a state where the pressure contact state of the tip of the lancet device with the inner circumferential face of the blood-collection position indicator is released.

When such a blood-collection position indicator 19 is applied, for example, to the leading-end member 93 with an elliptical end face of a lancet device as shown in FIG. 20A, the side ends of the elliptical leading-end member 93 in the major axis direction are brought into contact with and are pressed against the inner circumferential face except for the groove 191c of the base 191, thus attaching the blood-collection position indicator 19 to the leading-end member 93. When the leading-end member 93 is to be detached from the blood-collection position indicator 19, the leading-end member 93 is rotated, so that one of the side ends in the major axis direction, which are in contact with and are pressed against the inner circumferential face, comes to be positioned in the groove 191c as shown in FIG. 20B. When the one of the side ends in the major axis direction is positioned in the groove 191c, the pressure contact state of the side ends in the major axis direction with the inner circumferential face is released. Consequently, the leading-end member 93 can be detached easily. The other application methods are the same as in the embodiments A-1 and A-10. The number of grooves is not particularly limited as long as at least one groove is provided as described above.

Embodiment A-12

Figure 21:
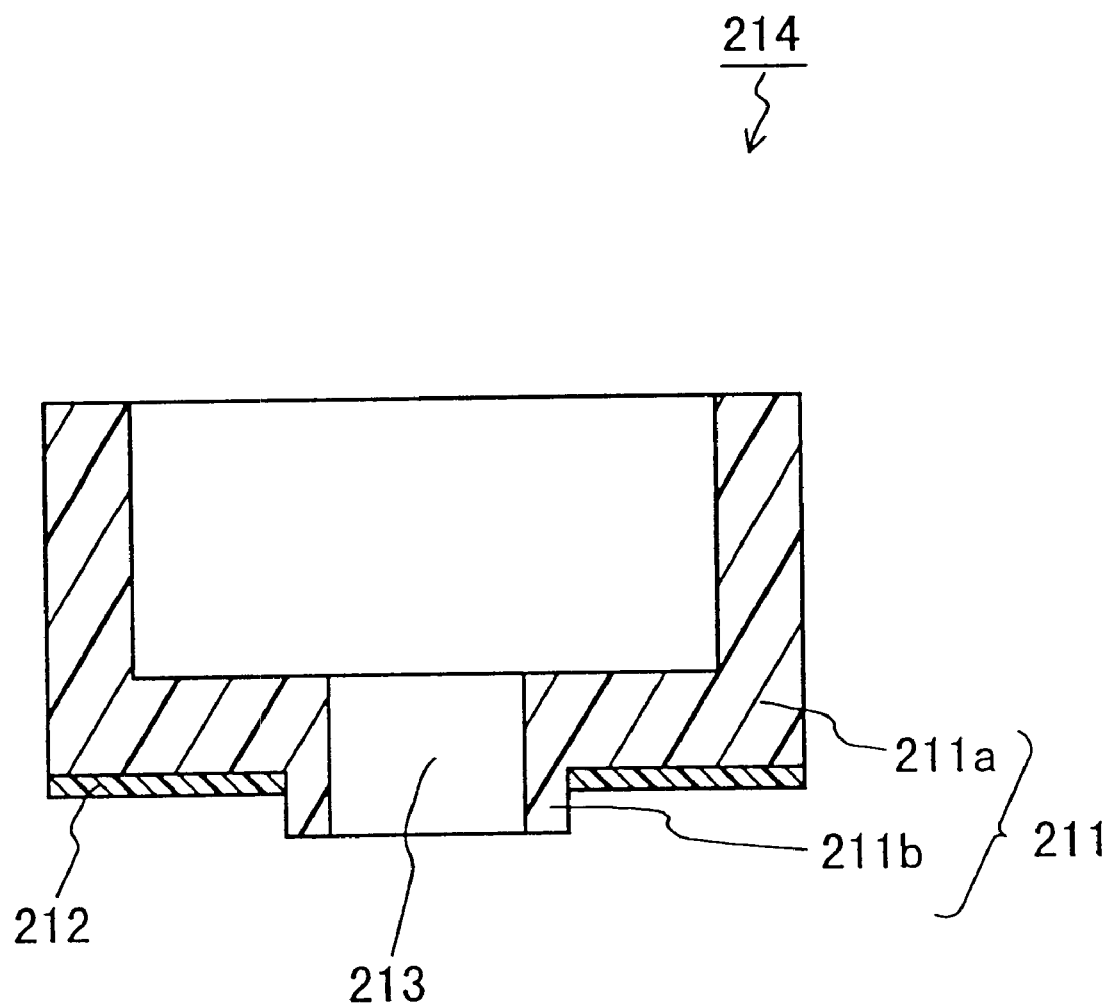
FIG. 21 is a sectional view showing a further embodiment of the first blood-collection position indicator according to the present invention.

FIG. 21 shows an example of a blood-collection position indicator having an annular protruding portion surrounding a through hole on a surface to be positioned to face the skin. FIG. 21 is a sectional view of the blood-collection position indicator. As shown in the figure, the blood-collection position indicator 214 includes a base 211 and an adhesive layer 212. The base 211 includes a main body 211a having a cylindrical shape with a bottom and an annular protruding portion 211b provided downward at substantially the center of the outer bottom face. A through hole 213 is formed of an inner space of the annular protruding portion 211b and a hole provided at substantially the center of the bottom of the main body. This through hole 213 serves as a blood collection hole. On the outer bottom face of the main body 211a, an adhesive layer 212 is formed.

In the blood-collection position indicator 214, the annular protruding portion 211b has a height, for example, in the range between 0.2 and 0.4 mm and its annular portion has a width, for example, in the range between 0.1 and 0.5 mm.

Figure 22:
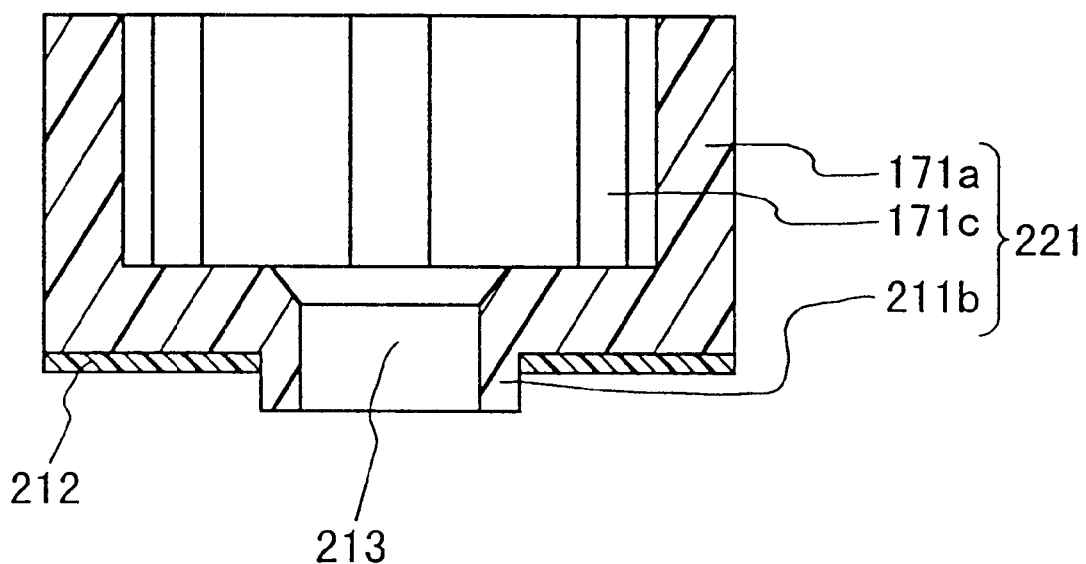
FIG. 22 is a sectional view showing still another embodiment of the first blood-collection position indicator according to the present invention.

The form with an annular protruding portion surrounding a through hole also can be applied, for example, to the blood-collection position indicator (see FIGS. 17A and 17B) having the grooves described in the embodiment A-10. This example is shown with a sectional view in FIG. 22. In FIG. 22, the same parts as those in FIGS. 17A, 17B, and 21 are indicated with the same numerals and characters. As shown in the figure, a through hole 213 of this blood-collection position indicator 224 may include a portion with a tapered shape expanding toward the inner portion of the cylindrical body. The number of grooves is not particularly limited as long as at least one groove is provided as described above.

The first blood-collection position indicator of the present invention is not limited to the above-mentioned respective embodiments at all. The shape of the blood-collection position indicator also is not particularly limited as long as the blood-collection position indicator can be attached to the tip of a lancet device. In the present invention, the respective configurations described separately in the above-mentioned embodiments may be combined.

Descriptions in the following embodiments B-1 to B-6 are directed to examples of the second blood-collection position indicator of the present invention.

Embodiment B-1

Figure 24A:
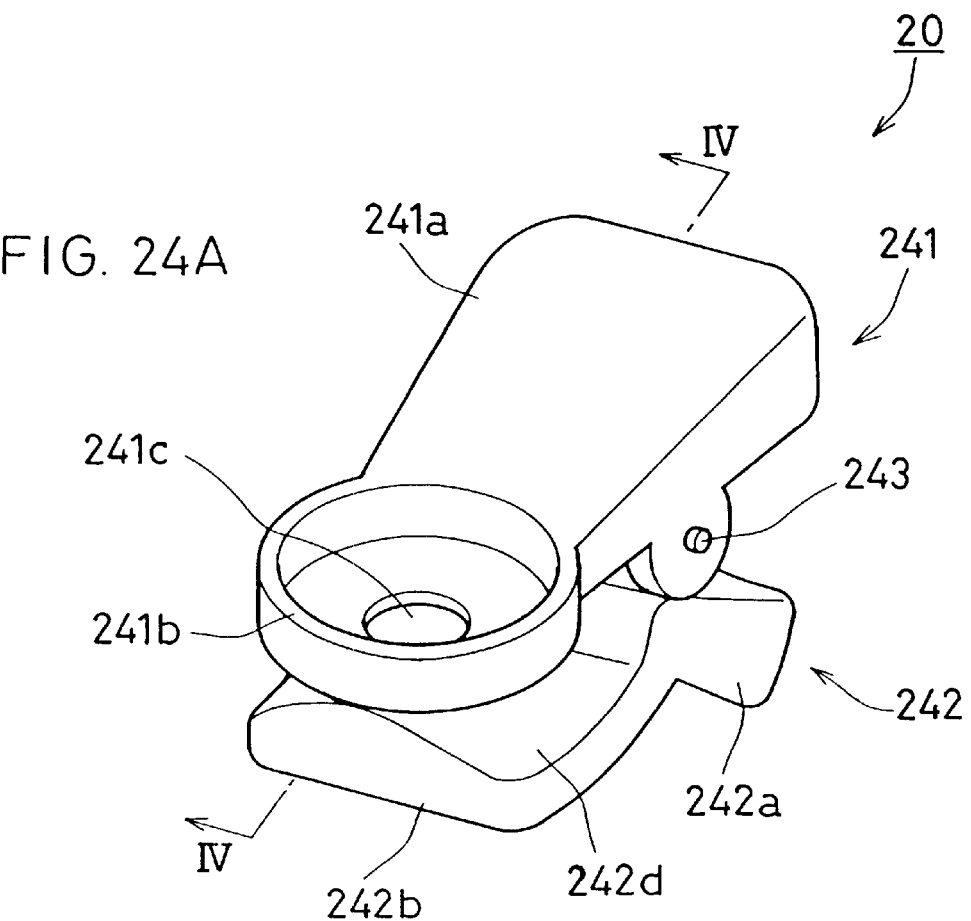
FIGS. 24A and 24B are perspective views showing an embodiment of the second blood-collection position indicator according to the present invention.
Figure 24B:
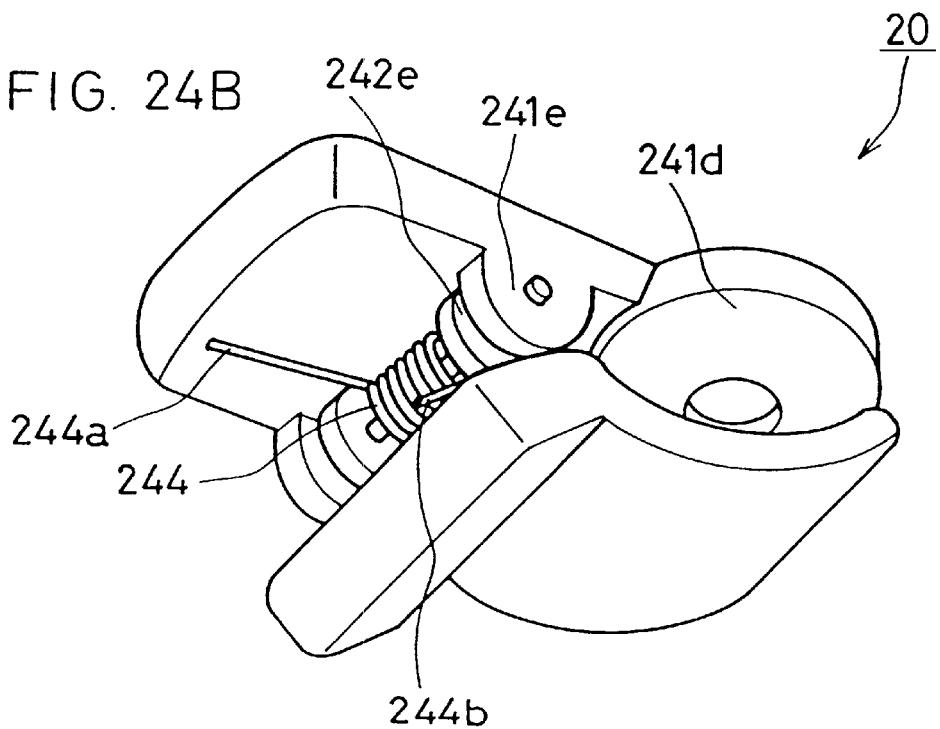
Figure 25:
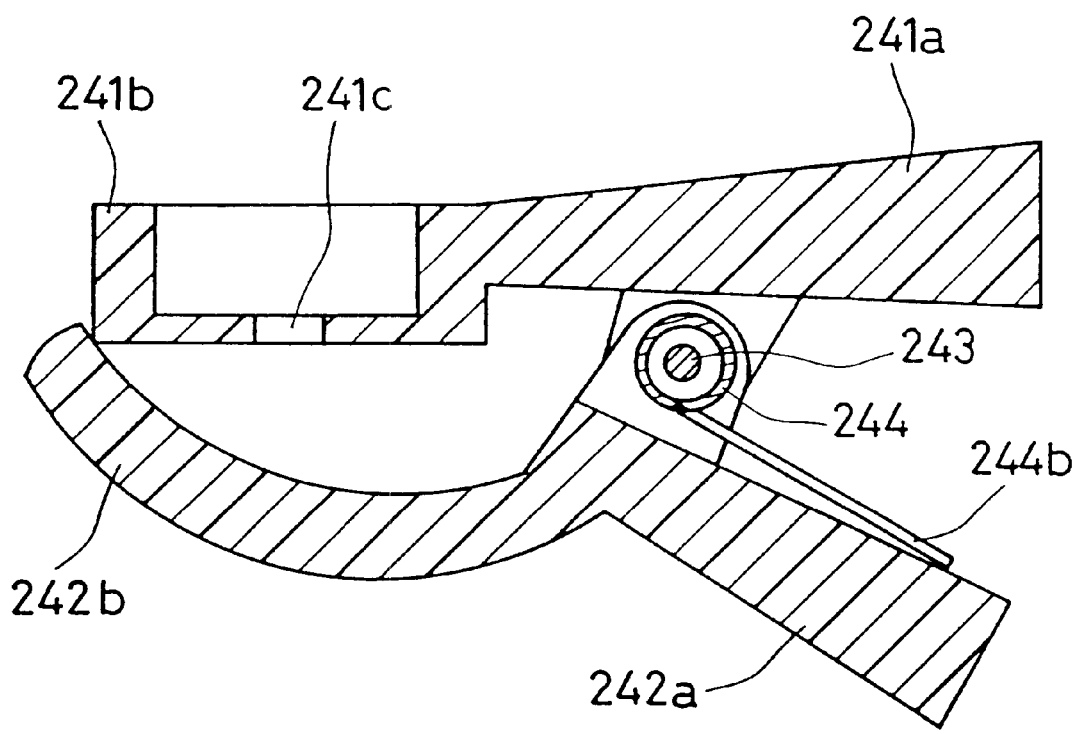
FIG. 25 is a sectional view of the blood-collection position indicator according to the embodiment.

FIGS. 24A, 24B, and 25 show an example of the second blood-collection position indicator according to the present invention. FIGS. 24A and 24B are perspective views of the blood-collection position indicator. FIG. 25 is a sectional view taken in the IV—IV direction in FIG. 24A. In FIG. 25, the same parts as those in FIGS. 24A and 24B are indicated with the same numerals and characters. As shown in the figures, this blood-collection position indicator 20 includes a pair of clip members 241 and 242 combined with an axis 243. A first clip part 241b and a second clip part 242b are provided on one side with respect to the axis 243 as the center, and a first grip part 241a and a second grip part 242a are provided on the other side. The first clip part 241b (on the upper side in FIG. 24A) is a cylindrical body with a bottom and to its side face, the end portion of the first grip part 241a is connected, thus forming both in one body. At substantially the center of the bottom of the cylindrical body 241b, a through hole 241c for blood collection is formed. The inner space of the cylindrical body 241b forms a concave portion, into which the tip of a lancet device is inserted. The outer bottom face of the cylindrical body 241b serves as a surface 241d to be brought into contact with the skin. The second clip part 242b has an inner surface (a surface to be brought into contact with the skin) 242d curved in a concave shape so as to be placed along the shape of a finger. The first grip part 241a has a pair of semicircular protrusions 241e at the ends in its width direction. The second grip part 242a also has a pair of semicircular protrusions 242e provided so as to be positioned adjacent to inner faces of the semicircular protrusions 241e. One axis 243 passes through these four semicircular protrusions to combine the pair of clip members 241 and 242. The respective protrusions 241e, 242e contact with the respective oppose grip parts to form supporting points. A spring 244 is wound around the axis 243. An end 244a of the spring 244 presses against the opposed surface of the first grip part 241a and the other end 244b presses against the opposed surface of the second grip part 242a. Thus, the clip parts 241b and 242b are urged to be in a closed state. In FIG. 25, the same parts as those in FIGS. 24A and 24B are indicated with the same numerals and characteristics.

The material of the clip members is not particularly limited. Examples of the material include plastics such as polyester, polypropylene, polystyrene, polycarbonate, or the like, metal such as stainless steel, aluminum, or the like, vinyl chloride, or the like.

The size of the blood-collection position indicator 20 is not particularly limited, but for example, its overall length is in the range between 30 and 50 mm and its overall width is in the range between 5 and 30 mm. The first clip part 241b has, for example, a height in the range between 1 and 10 mm, an outer diameter in the range between 5 and 20 mm, and an inner diameter in the range between 3 and 18 mm, and its bottom has a thickness in the range between 0.1 and 5 mm, and its blood collection hole 241c has a diameter in the range between 0.5 and 8 mm. The second clip part 242b has, for example, a width in the range between 5 and 20 mm, a length in the range between 15 and 30 mm, and a thickness in the range between 1 and 10 mm.

Setting of the size of the blood collection hole 241c enables, for example, quantitativity to be provided. For example, when blood in the range between 3 and 10 $\mu$l is to be collected, the blood collection hole 241c has a volume in the range between $3\times10^{-3}$ and 0.01 cm$^3$ and a diameter in the range between 2.8 and 3.6 mm, and the bottom of the cylindrical body has a thickness in the range between 0.5 and 1 mm.

Lancet devices used together with such a blood-collection position indicator 20 include, for example, one shown in FIG. 2 and can be used as described above.

When the lancet device 2 with the aforementioned size is used, the first clip part 241b has, for example, a height in the range between 0.1 and 5 mm, an outer diameter in the range between 5 and 20 mm, an inner diameter in the range between 3 and 18 mm, and its bottom has a thickness in the range between 0.1 and 5 mm, and the blood collection hole 241c has a diameter in the range between 0.5 and 8 mm.

For example, the lancet device 2 and the blood-collection position indicator 20 are used as follows. Initially, the grip parts 241a and 242a of the blood-collection position indicator 20 are held by hand and are pressed inward to open up the space between the clip parts 241b and 242b. Then, a finger is put into the space. After that, the blood collection hole 241c is positioned in a target blood collection site and the grip parts 241a and 242a are released. Since the clip parts 241b and 242b are urged to close by the spring 244, the blood-collection position indicator 20 is fixed sufficiently to the blood collection site of the finger.

The leading-end member 22 of the lancet device 2 set as described above is inserted into the concave portion (the attachment part) of the first clip part 241b of the blood-collection position indicator 20.

In this state, the lancet is ejected from the lancet device 2 to puncture the skin and then the lancet device 2 is moved away from the skin. By the puncture, blood is pooled inside the first clip part 241b through the blood collection hole 241c. In this case, according to this blood-collection position indicator 20, the finger is held by a force applied to the clip parts 241b and 242b, blood can be congested in the blood collection site. Therefore, a sufficient amount of blood can be obtained easily, for example, without squeezing the finger. Furthermore, when the blood collection hole is formed corresponding to the blood amount required for a test (i.e. has a quantitative function), it can be confirmed beforehand whether the required amount of blood has been collected.

When a glucose content is measured using such a measuring instrument 6 (see FIG. 23) as described above, a patient recognizes the blood-collection position indicator 20 and brings the tip of the strip 61 of the measuring instrument 6 into contact with the blood collection hole 241c to allow blood to be absorbed by the capillary phenomenon. The blood is transported inside the strip 61, and in a reagent part, a reagent and glucose in the blood react with each other. After both are reacted with each other for a certain period, the meter 62 of the measuring instrument 6 detects the reactant of them automatically and computes it into a glucose concentration, which then is displayed on a monitor.

Embodiment B-2

Figure 26A:
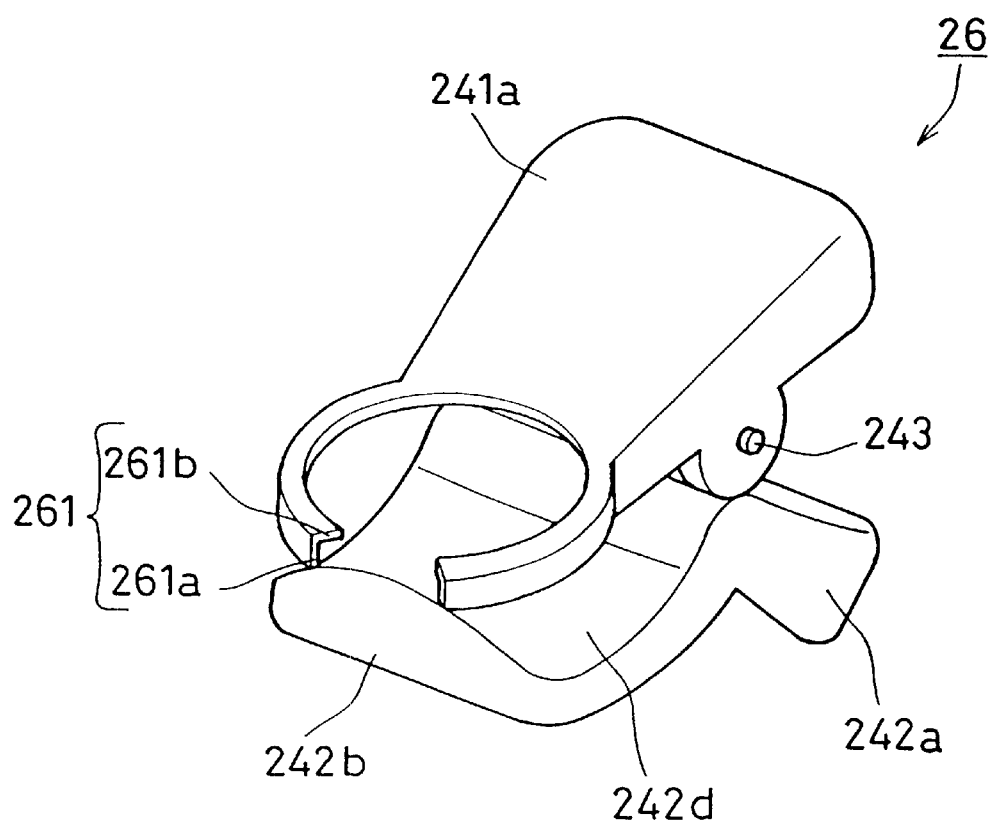
Figure 26B:
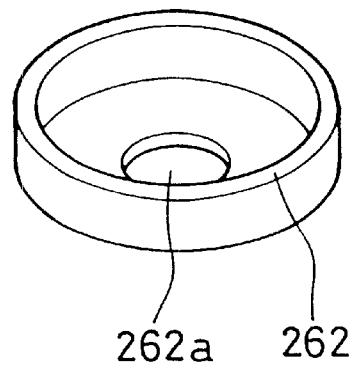

This example is an example of a blood-collection position indicator whose attachment part to be attached to the tip of a lancet device can be detached. This blood-collection position indicator includes an attachment member 262 shown in FIG. 26B and a main body 26 having a support 261 for the attachment member 262, which is shown in FIG. 26A. In the figures, the same parts as those in FIGS. 24A and 24B are indicated with the same numerals and characters.

In this main body 26, the support 261 for the attachment member 262 is formed instead of the first clip part 241b shown in FIGS. 24A and 24B. This support 261 has a substantially U-shaped planar shape. The support 261 has a reversed-L cross-section and includes a supporting body 261a and an edge portion 261b. On the other hand, the attachment member 262 has a cylindrical shape with a bottom and a through hole 262a for blood collection at substantially the center of the bottom. The outer bottom face of the attachment member 262 serves as the surface to be brought into contact with the skin.

Figure 27A:
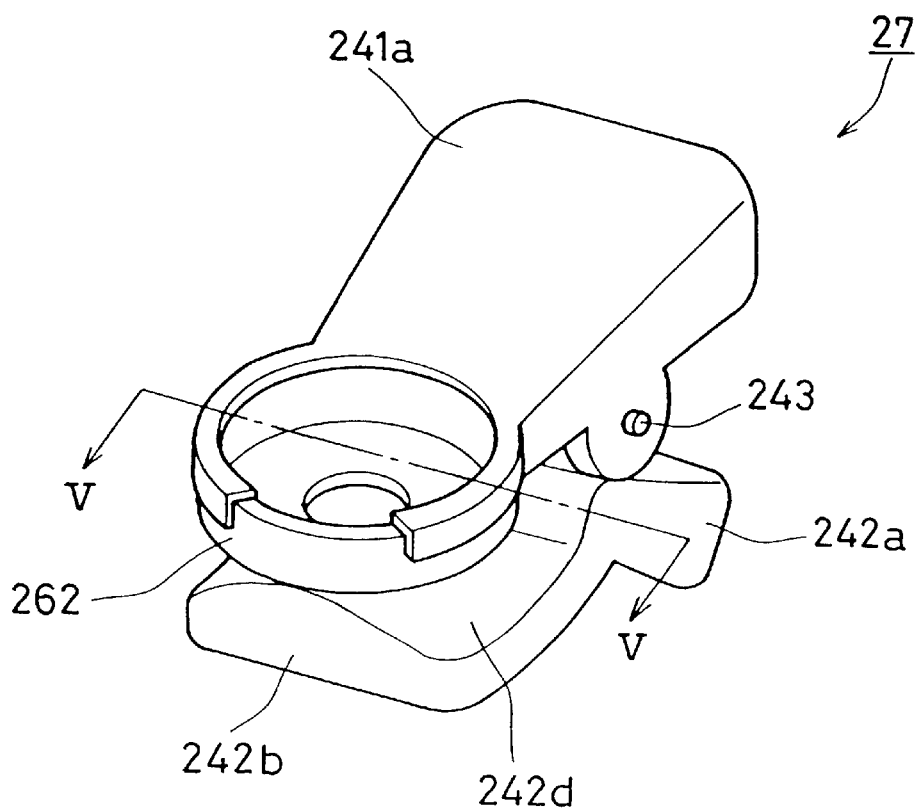
FIG. 27A is a perspective view showing the blood-collection position indicator according to the embodiment and FIG. 27B is a sectional view thereof.
Figure 27B:
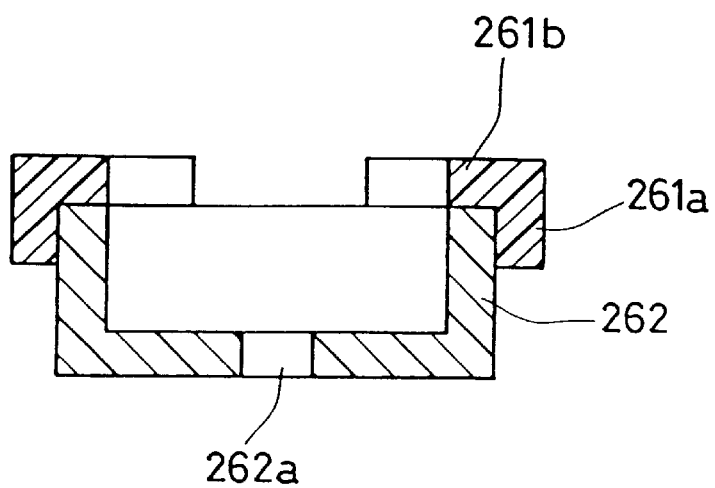

FIGS. 27A and 27B show a blood-collection position indicator constructed by combining the attachment member 262 into the main body 26. FIG. 27A is a perspective view of the blood-collection position indicator 27. FIG. 27B is a sectional view taken in the V—V direction of the portion where the attachment member 262 is inserted into the support 261 in FIG. 27A. The blood-collection position indicator 27 is used with the attachment member 262 being inserted into the support 261 from the opening of the U-shaped portion. After the blood-collection position indicator 27 is used, the attachment member 262 is detached and for the next application, the attachment member sterilized by wash or a new attachment member may be attached. In this manner, when the attachment member 262 is combined into the main body 26, a concave portion is formed in the clip part and the tip of a lancet device is attached to the concave portion. This blood-collection position indicator 27 can be used as in the embodiment B-1 except that the attachment member can be attached to and detached from the support.

In this embodiment, the support 261 has the edge portion 261b. Therefore, when a finger is held between the second clip part 242b and the attachment member 262 set in the main body 26, the attachment member 262 is not detached from the support 261 even when the attachment member 262 is pressed against the finger by the force applied by a spring. The shape of this support is not limited to that in this embodiment. For example, the support is not necessarily required to have the edge portion as long as it can support the attachment member sufficiently and the attachment member is not detached when a finger is held.

Descriptions in the following embodiments B-3 to B-6 are directed to examples of the attachment part, to which the tip of a lancet device is attached, in the second blood-collection position indicator according to the present invention. The forms of the attachment part described below can be applied to the first clip part in the integrated-type blood-collection position indicator according to the embodiment B-1 and the removable attachment member according to the embodiment B-2. The following attachment parts can be used as in the embodiment B-1 or B-2 as long as no specific description is provided. Therefore, in the embodiments B-3 to B-6, the "attachment part" indicates the first clip part and the removable attachment member.

Embodiment B-3

Figure 28A:
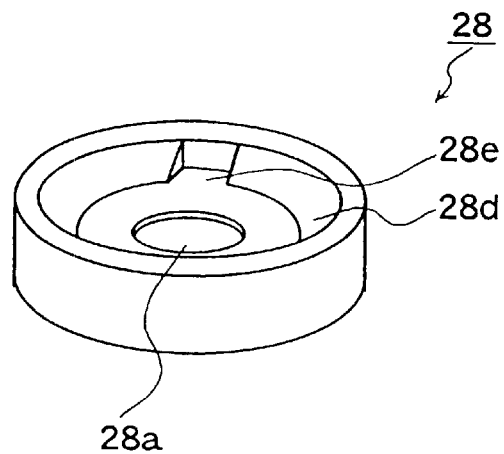
FIG. 28A is a perspective view showing another embodiment of the second blood-collection position indicator according to the present invention.
Figure 28B:
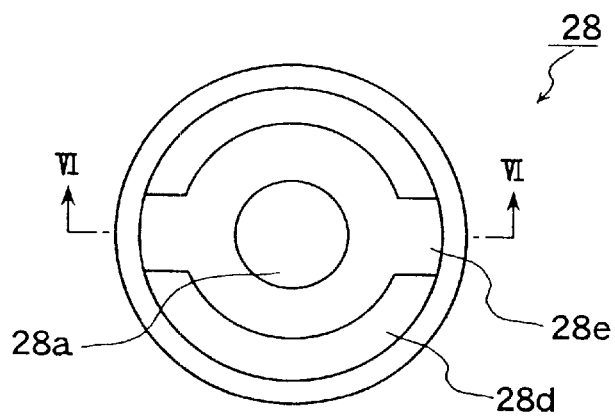
FIG. 28B is a plan view thereof.
Figure 28C:
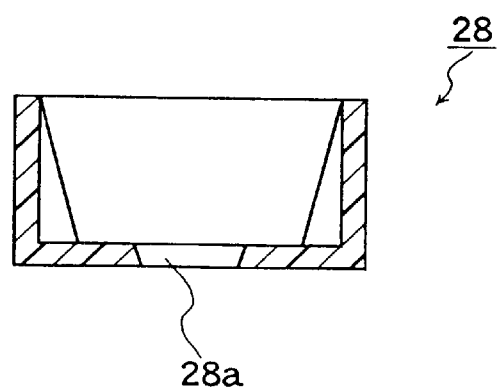
FIG. 28C is a sectional view thereof.

FIGS. 28A, 28B, and 28C show an example of an attachment part that can be applied to any of lancet devices with tips having circular and rectangular shapes. FIG. 28A is a perspective view of this attachment part, FIG. 28B is its plan view, and FIG. 28C is its sectional view taken in the VI—VI direction in the plan view. As shown in the figures, this attachment part 28 is a cylindrical body with a bottom. At substantially the center of the bottom, a through hole 28a for blood collection is formed. The inner space of the cylindrical body 28 forms a concave portion, into which the tip of the lancet device is inserted. The outer bottom face of the cylindrical body 28 serves as a surface to be brought into contact with the skin. The inner circumferential face of the cylindrical body 28 is a tapered surface 28d expanding toward the opening and is provided with two cut portions 28e.

In a blood-collection position indicator with such an attachment part 28, when it is applied to a leading-end member with a rectangular end face (see FIG. 9) of a lancet device, the leading-end member is inserted into the cut portions 28e, thus attaching the blood-collection position indicator to the leading-end member. Furthermore, when it is applied to a leading-end member with a round end face of a lancet device, the leading-end member may be inserted into the whole inner space of the attachment part 28. The other application methods are the same as in the embodiments B-1 and B-2.

Embodiment B-4

Figure 29A:
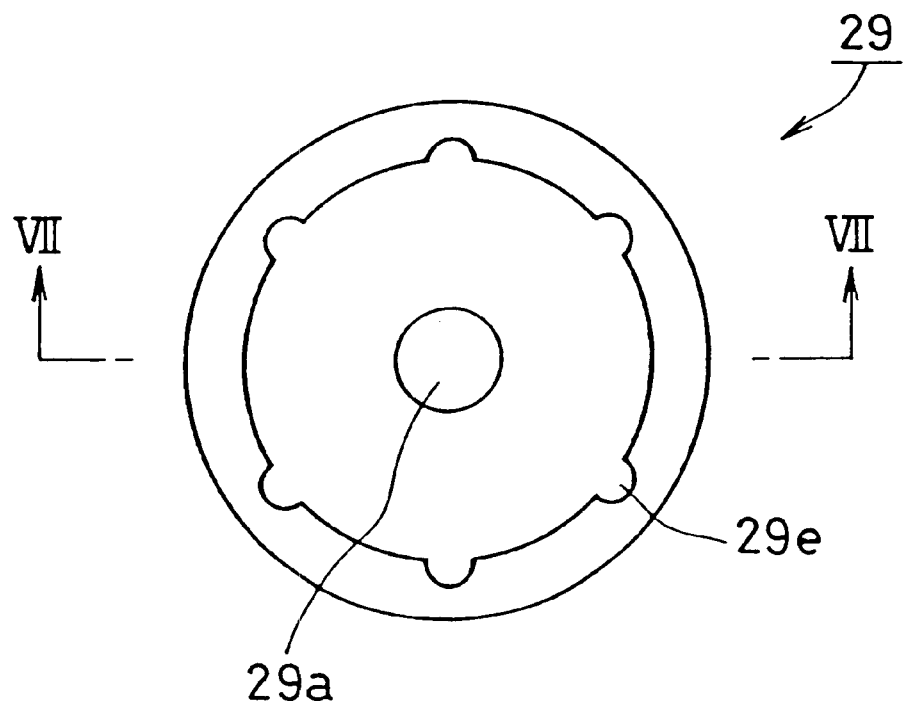
FIG. 29A is a plan view showing a further embodiment of the second blood-collection position indicator according to the present invention.
Figure 29B:
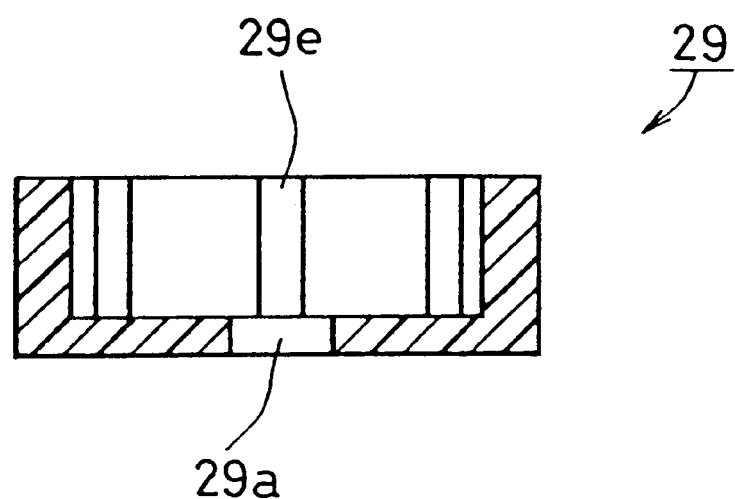
FIG. 29B is a sectional view thereof.

FIGS. 29A and 29B show an example of an attachment part useful for a lancet device with a tip having a rectangular shape. FIG. 29A is a plan view of this attachment part and FIG. 29B is a sectional view taken in the VII—VII direction in the plan view. As shown in the figures, this attachment part 29 is a cylindrical body with a bottom. At substantially the center of the bottom, a through hole 29a for blood collection is formed. The inner space of the cylindrical body 29 forms a concave portion, into which the tip of the lancet device is inserted. The outer bottom face of the cylindrical body 29 serves as a surface to be brought into contact with the skin. In the depth direction of the inner circumferential face of the cylindrical body 29, six grooves 29e with a semicircular cross-section are equally spaced.

Figure 30A:
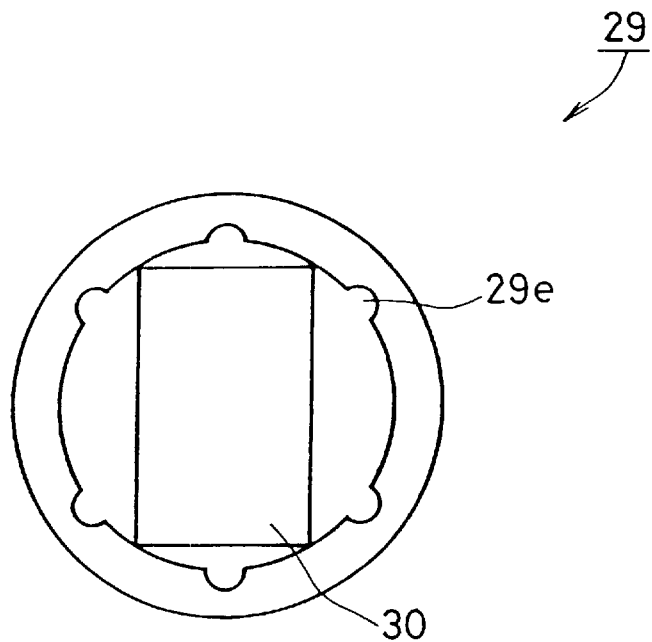
FIG. 30A is a plan view showing a state where the lancet device is brought into contact with and is pressed against the inner circumferential face of an attachment part in the second blood-collection position indicator according to still another embodiment of the present invention.
Figure 30B:
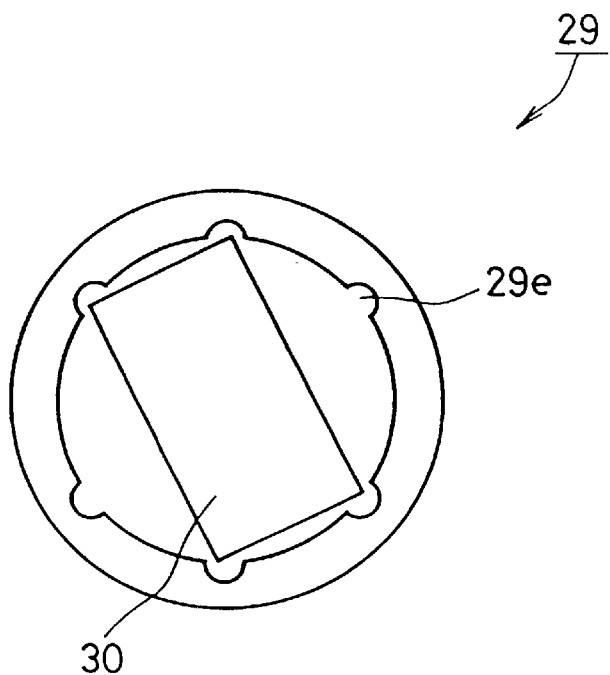
FIG. 30B is a plan view showing a state where the press contact state of the tip of the lancet device with the inner circumferential face is released.

When a blood-collection position indicator with such an attachment part 29 is applied, for example, to the leading-end member with a rectangular end face (see FIG. 9) of a lancet device, as shown in the plan view in FIG. 30A, the four corners of the leading-end member 92 are brought into contact with and are pressed against the inner circumferential face except for the grooves 29e of the cylindrical body 29, thus attaching the blood-collection position indicator to the leading-end member 92. When the leading-end member 92 is to be detached from the attachment part 29, as shown with the plan view in FIG. 30B, the leading-end member 92 is rotated, so that its four corners come to be positioned in the grooves 29e. When the four corners are positioned in the grooves 29e, the pressure contact state between the four corners and the inner circumferential face is released. Consequently, the leading-end member 92 can be detached easily. The other application methods are the same as in the embodiments B-1 and B-2.

The number of the grooves 29e are not particularly limited, but is, for example, in the range between 1 and 12, preferably in the range between 3 and 12, further preferably in the range between 4 and 8, and particularly preferably 6. The positions of the grooves 29e can be determined suitably according to, for example, the shape of the tip of the leading-end member to be used or the like. When the grooves are provided in a plurality of positions, the selection of the positions of the grooves, from those positions, corresponding to the shape of the tip of a leading-end member enables the attachment part 29 to be applied to leading-end members with various shapes. The shape of the grooves is not particularly limited, but is preferred to have a cross-section with a U shape, a circular arc shape, a V shape, a rectangular shape with one side being open, or the like.

Embodiment B-5

Figure 31:
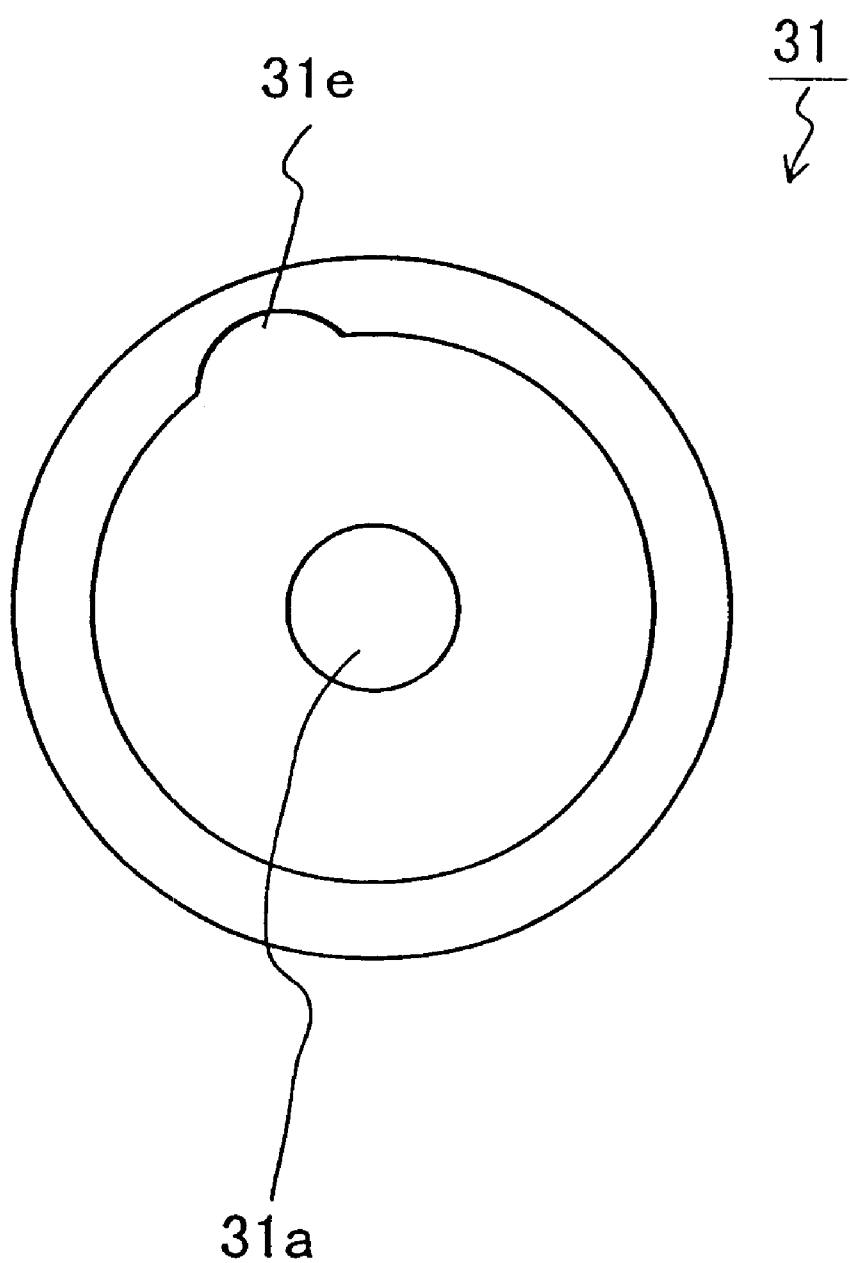
FIG. 31 is a plan view showing yet another embodiment of the second blood-collection position indicator according to the present invention.

FIG. 31 shows a plan view of an example of an attachment part useful for a lancet device with a tip having an elliptical shape. As shown in the figure, this attachment part 31 is a cylindrical body with a bottom. At substantially the center of the bottom, a through hole 31a for blood collection is formed. The inner space of the cylindrical body 31 forms a concave portion, into which the tip of the lancet device is inserted. The outer bottom face of the cylindrical body 31 serves as a surface to be brought into contact with the skin. In the depth direction of the inner circumferential face of the cylindrical body 31, a groove 31e with a semicircular cross-section is provided.

Figure 32A:
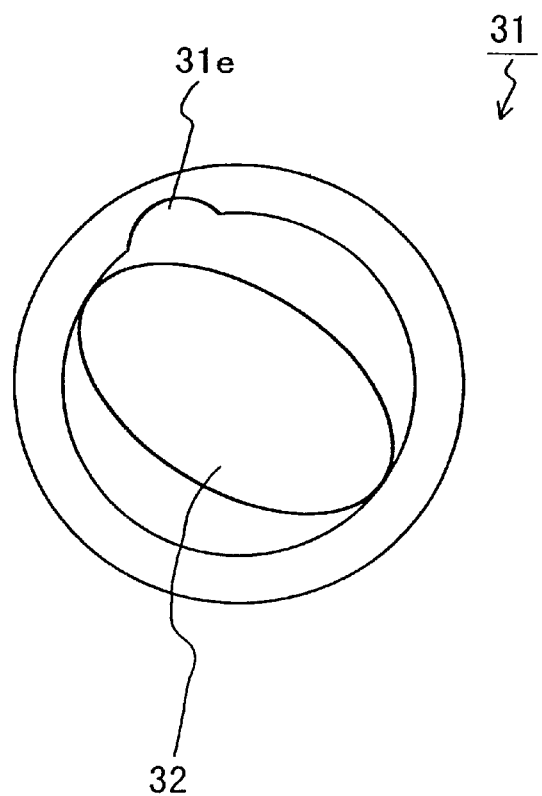
FIG. 32A is a plan view showing a state where the lancet device is brought into contact with and is pressed against the inner circumferential face of an attachment part in the blood-collection position indicator according to the embodiment.
Figure 32B:
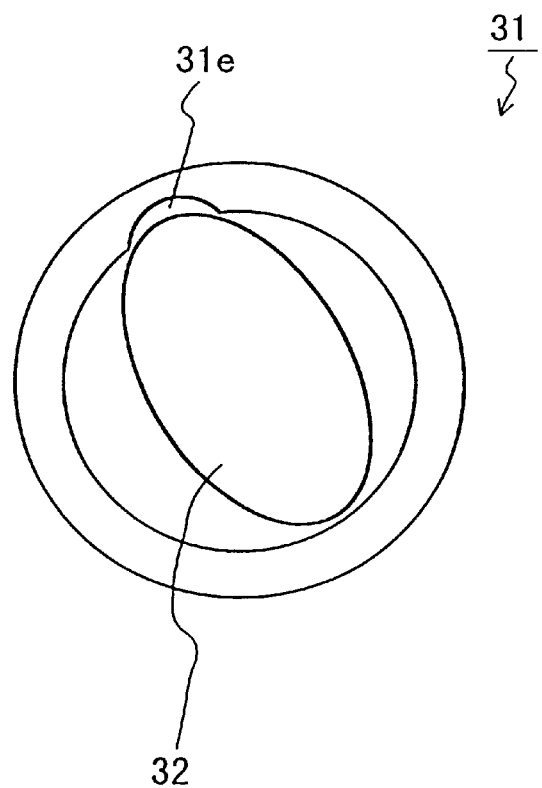
FIG. 32B is a plan view showing a state where the pressure contact state of the tip of the lancet device with the inner circumferential face is released.

In a blood-collection position indicator with such an attachment part 31, for example, when it is applied to the leading-end member 93 with an elliptical end face of a lancet device as shown with the plan view in FIG. 32A, the side ends of the leading-end member 93 in the major axis direction are brought into contact with and are pressed against the inner circumferential face except for the groove 31e of the cylindrical body 31, thus attaching the blood-collection position indicator to the leading-end member 93. When the leading-end member 93 is to be detached from the attachment part 31, the leading-end member 93 is rotated, so that one of the side ends in the major axis direction, which are in contact with and are pressed against the inner circumferential face, comes to be positioned in the groove 31e as shown with the plan view in FIG. 32B. When the one of the side ends in the major axis direction is positioned in the groove 31e, the pressure contact state between the side ends in the major axis direction and the inner circumferential face is released. Consequently, the leading-end member 93 can be detached easily. The other application methods are the same as in the embodiments B-1 and B-2. The number of grooves is not particularly limited as long as at least one groove is provided as described above.

Embodiment B-6

Figure 33:
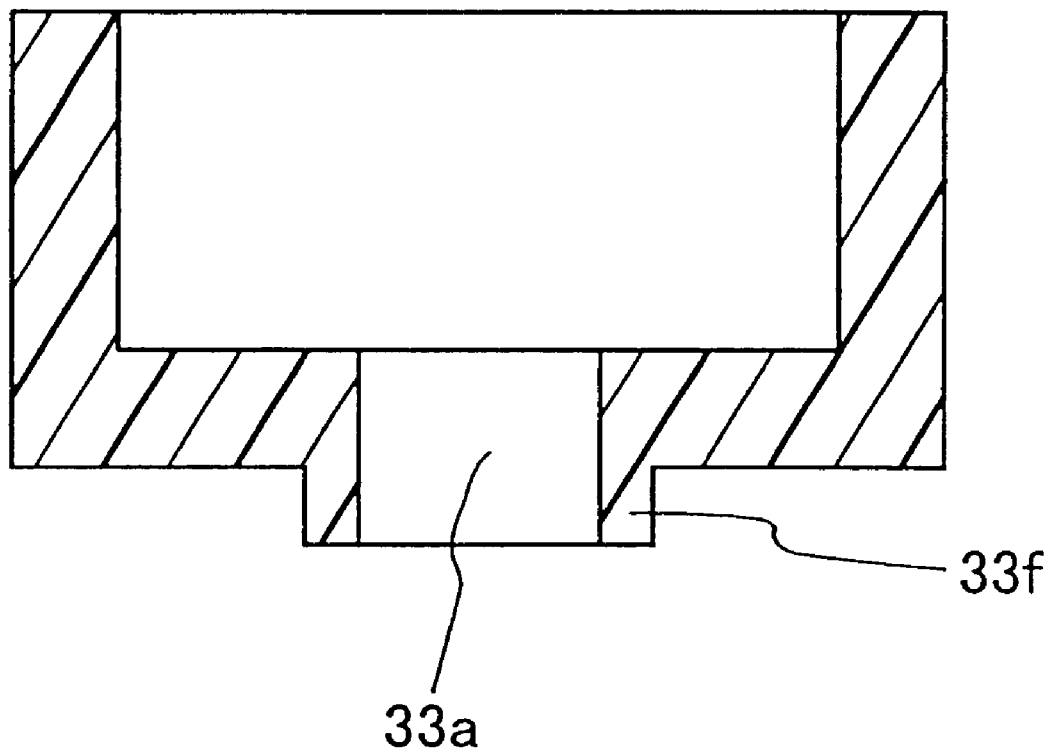
FIG. 33 is a sectional view showing a further embodiment of the second blood-collection position indicator according to the present invention.

FIG. 33 shows an sectional view illustrating an example of an attachment part having an annular protruding portion surrounding a through hole on a surface to be brought into contact with the skin. As shown in the figure, this attachment part 33 is a cylindrical body with a bottom. At substantially the center of the bottom, a through hole 33a for blood collection is formed. The inner space of the cylindrical body 33 forms a concave portion, into which the tip of a lancet device is inserted. The outer bottom face of the cylindrical body 33 is provided with an annular protruding portion 33f surrounding the through hole 33a. The bottom face of the annular protruding portion 33f and the outer bottom face of the cylindrical body 33 serve as surfaces to be brought into contact with the skin.

The annular protruding portion 33f has a height, for example, in the range between 0.2 and 0.4 mm and its annular portion has a width, for example, in the range between 0.1 and 0.5 mm.

Figure 34:
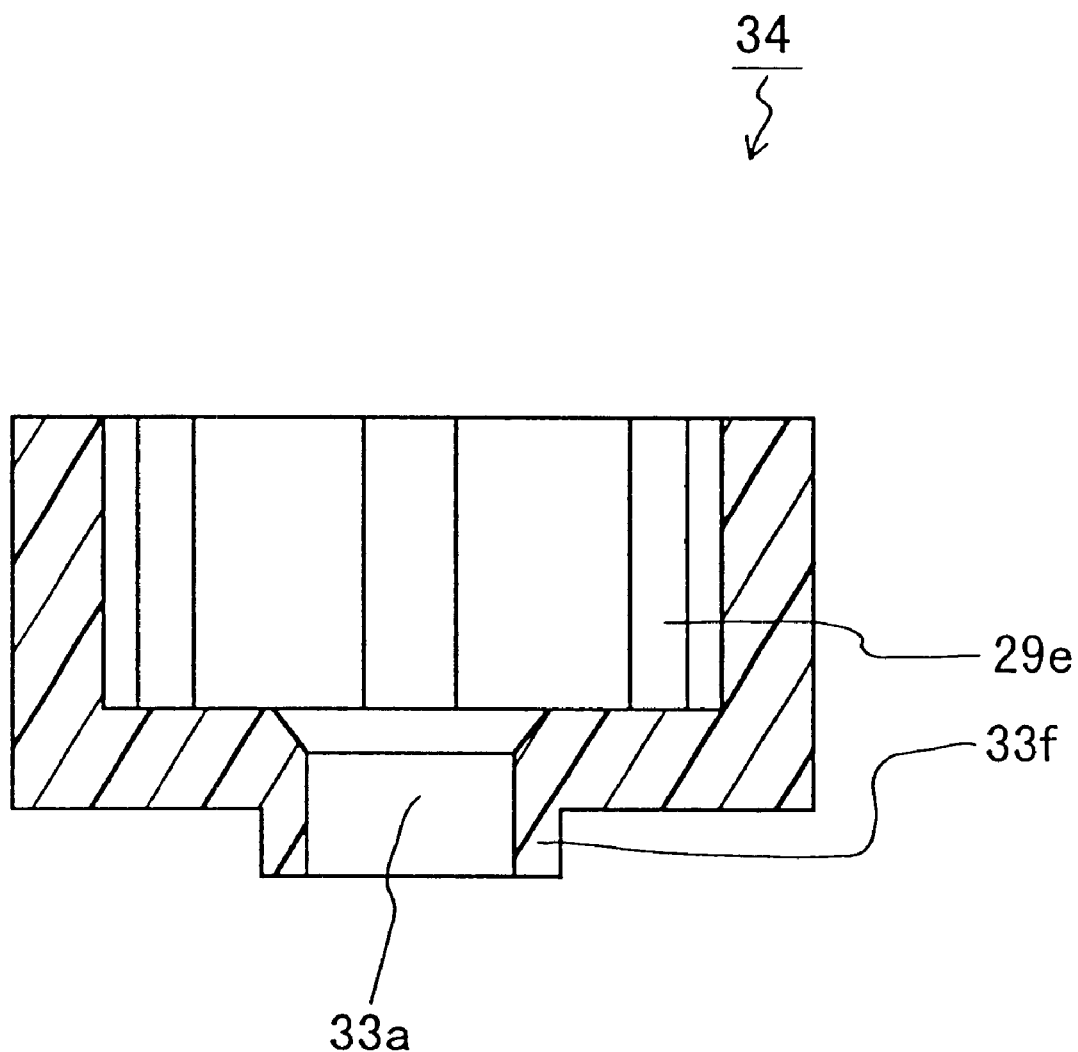
FIG. 34 is a sectional view showing still another embodiment of the second blood-collection position indicator according to the present invention.

The form with the annular protruding portion 33f surrounding the through hole also can be applied, for example, to the attachment part (see FIGS. 29A and 29B) having grooves described in the embodiment B-4. This example is shown with a sectional view in FIG. 34. In FIG. 34, the same parts as those in FIGS. 29A, 29B, and 33 are indicated with the same numerals and characters. As shown in the figure, a through hole 33a may include a portion with a tapered shape expanding toward the inner portion of the attachment part 34. The number of the grooves is not particularly limited as long as at least one groove is provided as described above.

In the embodiments as described above, a spring is used as a member for providing a force to bring the pair of clip parts into a closed state (with the clip parts being pressed against each other). However, the member is not limited to the spring as long as the clip parts are pressed against each other. For instance, the pair of clip parts may be formed of resin or the like to form one body and may be pressed against each other by elasticity of the resin or the like.

The shape of the grip parts is not particularly limited. However, it is preferable that for example, antislipping concave and convex portions are formed on their outer surfaces.

The second blood-collection position indicator of the present invention is not limited to the above-mentioned respective embodiments at all and its shape also is not particularly limited. In the present invention, the respective configurations described separately in the above-mentioned embodiments may be combined.

As described in the above, when using the blood-collection position indicators of the present invention, for example, without relying on the visual sense, the blood collection site can be recognized through the blood-collection position indicator. Consequently, blood can be collected easily and quickly. Such blood-collection position indicators are useful for blood collection at home, particularly for blood collection by the visually handicapped by themselves.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A blood-collection position indicator, comprising a pair of clip members,
   wherein the pair of clip members are in contact with each other at a supporting point and include clip parts for holding skin, which are formed on one side with respect to the supporting point as the center, and grip parts formed on the other side, respectively, the clip parts are urged to be in a closed state, at least one of the clip parts has an attachment part to be attached to a tip of a lancet device including a lancet, and the attachment part is provided with a blood collection hole, through which the lancet can pass.

2. The blood-collection position indicator according to claim 1, wherein at least one of the clip parts is provided with a concave portion, the bottom of the concave portion is provided with a through hole serving as the blood collection hole, and the tip of the lancet device is attached to an inner space of the concave portion.

3. The blood-collection position indicator according to claim 2, wherein the concave portion has an inner circumferential face provided with at least one groove along a depth direction, a part of a peripheral surface of the tip of the lancet device is brought into contact with and is pressed against a portion except for the groove of the inner circumferential face, thus attaching the attachment part to the tip of the lancet device in a pressure contact state, and the part being in contact with and being pressed against the portion is movable to be positioned in the groove, thus releasing the pressure contact state.

4. The blood-collection position indicator according to claim 3, wherein the tip of the lancet device has a rectangular shape, and corners of the tip are brought into contact with and are pressed against the portion except for the groove of the inner circumferential face of the concave portion.

5. The blood-collection position indicator according to claim 3, wherein the tip of the lancet device has an elliptical shape, and side ends of the tip in a major axis direction are brought into contact with and are pressed against the portion except for the groove of the inner circumferential face of the concave portion.

6. The blood-collection position indicator according to claim 2, wherein the blood collection hole includes a portion with a tapered shape expanding in a direction away from the skin, in use.

7. The blood-collection position indicator according to claim 1, wherein the clip part having the blood collection hole is provided with an annular protruding portion surrounding the blood collection hole on a surface, of the clip part, to be brought into contact with the skin.

8. The blood-collection position indicator according to claim 1, wherein the blood collection hole has a quantitative function.

9. The blood-collection position indicator according to claim 1, wherein the attachment part can be detached.

* * * * *